(12) United States Patent
Gerard et al.

(10) Patent No.: US 6,503,498 B1
(45) Date of Patent: Jan. 7, 2003

(54) APOLIPOPROTEIN A-1 ADENOVIRUS VECTOR COMPOSITIONS AND METHODS

(75) Inventors: Robert D. Gerard; Robert S. Meidell, both of Dallas; John E. Willard, Grapevine, all of TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 08/224,595

(22) Filed: Apr. 5, 1994

Related U.S. Application Data

(63) Continuation-in-part of application No. 07/968,861, filed on Oct. 29, 1992, now abandoned.

(51) Int. Cl.$^7$ ........................ A61K 48/00; C12N 15/861

(52) U.S. Cl. ...................... 424/93.2; 435/320.1; 514/44

(58) Field of Search .............................. 424/93.21, 93.2; 514/44; 435/320.1

(56) References Cited

U.S. PATENT DOCUMENTS

| | | | |
|---|---|---|---|
| 4,960,700 A | * 10/1990 | Malfroy-Camine et al. ...... | 435/172.3 |
| 5,225,537 A | * 7/1993 | Foster ......................... | 530/380 |
| 5,434,058 A | * 7/1995 | Davidson .................... | 435/69.1 |
| 5,476,777 A | * 12/1995 | Holly et al. ................. | 435/214 |

OTHER PUBLICATIONS van Zonneveld et al., Journal of Cellular Biochemistry, 32:169–178 (1986).*
Kopfler et al., Circulation, 90:1319–1327 (1994).*
Perevozchikov et al., Dokl. Akad. Nauk., 335(5):646–649 (1994), abstract only.*
Orkin et al., "Report and recommendations of the panel to assess the NIH investment in research on gene therapy", issued by the U.S. National Institutes of Health, Dec. 7, 1995.*
Levrero et al., "Defective and nondefective adenovirus vectors for expressing foreign genes in vitro and in vivo", Gene 101: 195–202, 1991.*
Stratford–Perricaudet et al., "Gene transfer into animals: the promise of adenovirus", Human Gene Transfer 219: 51–61, 1991.*
Kowathanasis et al PNAS 10:6147, 1983, Oct. 1, 1997.*
Willard, JE et al., Circulation, 86(4Supp.1):I473 (1992).*
Nabel, EG et al., Circulation, 91(2):541–548 (1995).*
LaFont Lancet 346:1442–1443, 1995.*
Berkner, Kathleen L., "Development of Adenovirus Vectors for the Expression of Heterologous Genes," *BioTechniques*, 6(7):616–629, 1988.
Callow, Allan D., "The Vascular Endothelial Cell as a Vehicle for Gene Therapy," *J. Vasc. Surg.*, 11:793–798, 1990.

Dichek et al., "Retroviral Vector–Mediated In Vivo Expression of Low–Density–Lipoprotein Receptors in the Watanabe Heritable Hyperlipidemic Rabbit," *Somatic Cell and Molecular Genetics*, 17(3):287–301, 1991.
Eglitis and Anderson, "Retroviral Vectors for Introduction of Genes into Mammalian Cells," *BioTechniques*, 6(7):608–614, 1988.
Friedman et al., "Virus Infection of Endothelial Cells," *J. Infect. Dis.*, 143(2):266–273, 1981.
Ghosh–Choudhury and Graham, "Stable Transfer of a Mouse Dihydrofolate Reductase Gene Into a Deficient Cell Line Using Human Adenovirus Vector," *Biochem. Biophys. Res. Comm.*, 147(3):964–973, 1987.
Hofmann et al., "Overexpression of Low Density Lipoprotein (LDL) Receptor Eliminates LDL from Plasma in Transgenic Mice," *Science*, 239:1277–1281, 1988.
Jaffe et al., "Adenovirus–Mediated In Vivo Gene Transfer and Expression in Normal Rat Liver," *Nature Genetics*, 1:372–378, 1992.
Lemarchand et al., "Adenovirus–Mediated Transfer of a Recombinant Human $\alpha_1$–Antitrypsin cDNA to Human Endothelial Cells," *Proc. Natl. Acad. Sci. USA*, 89:6482–6486, 1992.
Merlo et al., "The Mouse int–2 Gene Exhibits Basic Fibroblast Growth Factor Activity in a Basic Fibroblast Growth Factor–Responsive Cell Line," *Cell Growth & Differentiation*, 1:463–472, 1990.
Nabel and Nabel, "Gene Transfer and Cardiovascular Disease," *TCM*, pp. 12–17, Jan./Feb., 1991.
Nabel et al., "Site–Specific Gene Expression in Vivo by Direct Gene Transfer into the Arterial Wall," *Science*, 249:1285–1288, 1990.
Petropoulos et al., "Using Avian Retroviral Vectors for Gene Transfer," *Journal of Virology*, 66(6):3391–3397, 1992.
Petropoulos and Hughes, "Replication–Competent Retrovirus Vectors for the Transfer and Expression of Gene Cassettes in Avian Cells," *Journal of Virology*, 65(7):3728–3737, 1991.
Prevec et al., "Use of Human Adenovirus–Based Vectors for Antigen Expression in Animals," *J. Gen. Virol.*, 70:429–434, 1989.

(List continued on next page.)

*Primary Examiner*—Scott D. Priebe
(74) *Attorney, Agent, or Firm*—Fulbright & Jaworski

(57) ABSTRACT

The present disclosure demonstrates the successful use of adenovirus mediated gene transfer to increase HDLc in mammalian cells and in mice. BALB/c mice were infected with recombinant adenovirus containing a gene encoding human apolipoprotein A-I (AdCMVApo-I). Immunoreactive apoA-I averaged 168 mg/dl 5 days after infection. HDLc was increased by 35% in infected mice. Lipoprotein analysis revealed that human apoA-I is incorporated into murine HDL particles, producing transient elevations of circulating HDLc of a magnitude correlated with important physiologic effects. Also disclosed are pharmacological preparations to be used to increase serum HDLc in a subject.

6 Claims, 14 Drawing Sheets

OTHER PUBLICATIONS

Rosenfeld et al., "In vivo Transfer of the Human Cystic Fibrosis Transmembrane Conductance Regulator Gene to the Airway Epithelium," *Cell*, 68:143–155, 1992.

Rosenfeld et al., "Adenovirus–Mediated Transfer of a Recombinant α1–Antitrypsin Gene to the Lung Epithelium in Vivo," *Science*, 252:431–434, 1991.

Stratford–Perricaudet et al., "Evaluation of the Transfer and Expression in Mice of an Enzyme–Encoding Gene Using a Human Adenovirus Vector," *Human Gene Therapy*, 1:241–256, 1990.

Stratford–Perricaudet et al., "Feasibility of Adenovirus–Mediated Gene Transfer in Vivo," *Bone Marrow Transplantation*, 9(Suppl. 1):151–152, 1992.

Wilson et al., "Retrovirus–Mediated Transduction of Adult Hepatocytes," *Proc. Natl. Acad. Sci. USA*, 85:3014–3018, 1988.

Wilson et al., "Hepatocyte–Directed Gene Transfer in Vivo Leads to Transient Improvement of Hypercholesterolemia in Low Density Lipoprotein Receptor–Deficient Rabbits," *J. Biolog. Chem.*, 267(2):963–967, 1992.

Wilson et al., "Correction of the Genetic Defect in Hepatocytes from the Watanabe Heritable Hyperlipidemic Rabbit," *Proc. Natl. Acad. Sci. USA*, 85:4421–4425, 1988.

Dzau et al., "Gene Therapy for Cardiovascular Disease," *Tibtech*, 11:205–210, 1993.

Herz, J. and Gerard R., "Adenovirus–Mediated Transfer of Low Density Lipoprotein Receptor Gene Acutely Accelerates Cholesterol Clearance in Normal Mice," *Proc. Natl. Acad. Sci. USA*, 90:2812–2816, 1993.

Ishibashi et al. "Hypercholesterolemia in Low Density Lipoprotein Receptor Knockout Mice and Its Reversal by Adenovirus–Mediated Gene Delivery," *J. Clin. Invest.* 92:883–894, 1993.

International Search Report, mailed Jan. 3, 1994.

Denèfle, et al., "Evaluation of Recombinant Adenovirus Vectors for Gene Therapy of Lipoprotein Disorders," *J of Cell. Biochem.*, Supplement 18–A:278, 1994.

Frolkis, V.V., et al., "Effect of transfer of human ApoA1 gene on development of dyslipoproteinemias in rats: Age peculiarities," *Arch. Gerontol. Geriatr.*, 13:225–236, 1991.

Gerard, R. and Meidell, R., "Adenovirus–Mediated Gene Transfer Into Vascular Cells," *J of Cell. Biochem.*, Supplement 18–A:264, 1994.

Kopfler, et al., "Adenovirus–Mediated Human Apolipoprotein A1 Gene Transfer Increases Circulating HDL Cholesterol in Mice," *Clin. Res.*, 41(2): 211A, 1993.

Lee, et al., "Adenoviral–Mediated Gene Transfer Into the Injured Rat Carotid Artery," *Supplement to Circulation*, 88 (4, part 2): I–371, abstract #1992.

March, et al., Gene Therapy To Block Restenosis Following Percutaneous Transluminal Coronary Angioplasty: Feasibility Of Strategies To Target Smooth Muscle Cells Using Adenoviral Vectors, *Supplement to Circulation*, 88 (4, part 2): I–371, abstract #1990.

Rubin et al., "Inhibition of early atherogenesis in transgenic mice by human apolipoprotein AI," *Nature*, 353:265–267, 1991.

Rubin, et al., "Prevention of Atherosclerosis in Transgenic Mice Which Over–Express Human Apolipoprotein," *J of Cell. Biochem.*, Supplement. 15A:202 B413, 1991.

Schneider and French, "The Advent of Adenovirus Gene Therapy for Cardiovascular Disease," *Circulation*, 88(4, part 1):1937–1942, 1993.

More Than It Can Bear, *Economist*, p. 86 (Jan. 29, 1994).

* cited by examiner

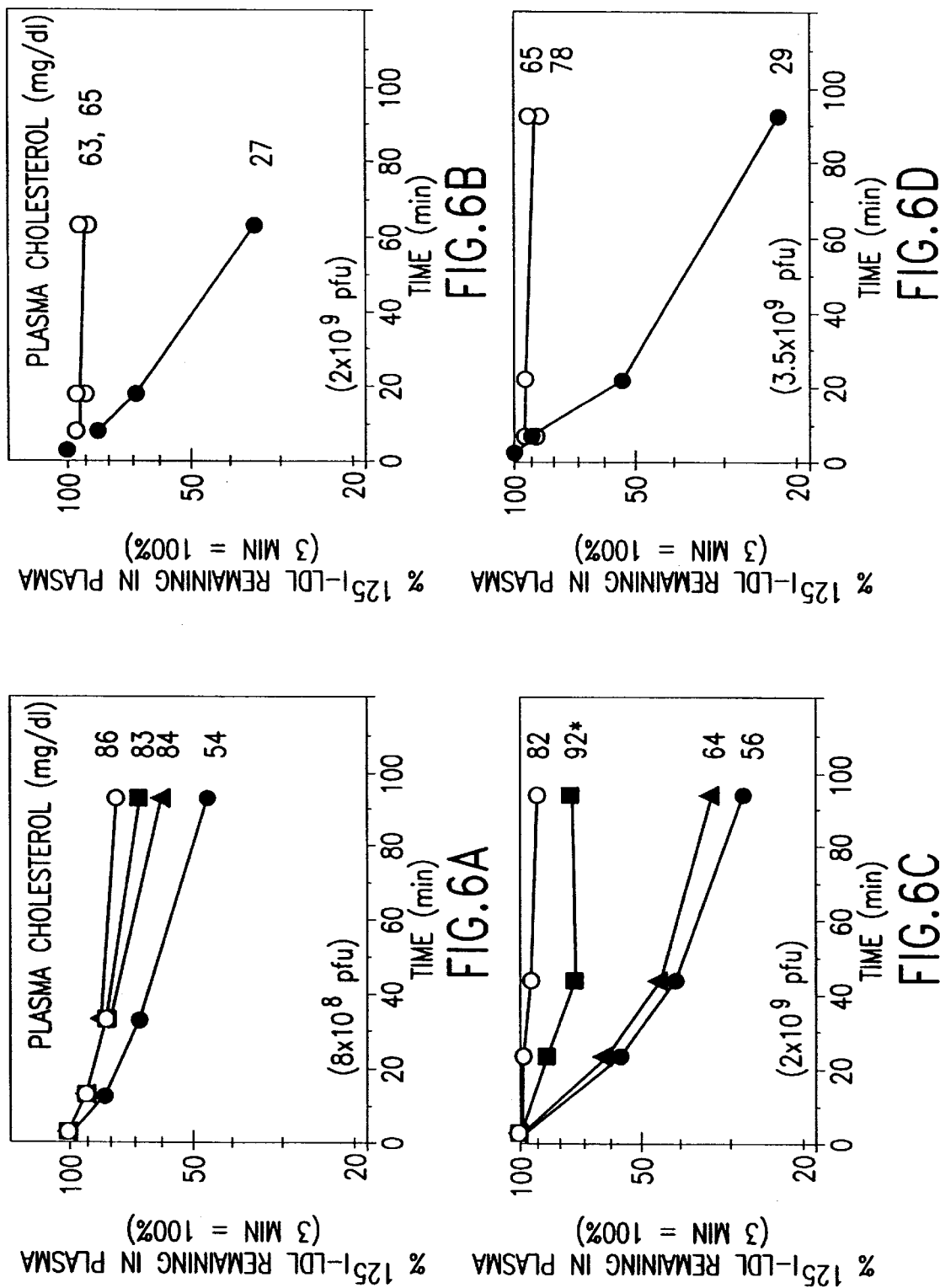

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 34 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

CGGCATTTCT GGCAGAGATC TGAACCCCCC CAGA      34

(2) INFORMATION FOR SEQ ID NO:2:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

TTTTCTAGAG CCTCACTGGG TGTTGAGCTT CTT      33

(2) INFORMATION FOR SEQ ID NO:3:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

TGGCAGCAAG ATGAACCCCC C      21

(2) INFORMATION FOR SEQ ID NO:4:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:4:

Trp Gln Gln Asp Glu Pro Pro
1         5

(2) INFORMATION FOR SEQ ID NO:5:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Gly Ala Arg Ser
1
```

(2) INFORMATION FOR SEQ ID NO:6:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
GGAGCCAGAT CT                                                    12
```

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
CAGAGATCTG AACCCCCC                                              18
```

(2) INFORMATION FOR SEQ ID NO:8:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Gln Arg Ser Glu Pro Pro
1               5
```

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
GGAGCCAGAT CTGAACCCCC C                                          21
```

-continued (2) INFORMATION FOR SEQ ID NO:10:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Gly Ala Arg Ser Glu Pro Pro
1           5

APOLIPOPROTEIN A-1 ADENOVIRUS VECTOR COMPOSITIONS AND METHODS

This application is a continuation-in-part of copending application Ser. No. 07/968,861, filed Oct. 29, 1992, now abandoned. The entire text and figures of the above-referenced disclosure is specifically incorporated herein by reference without disclaimer.

The government owns rights in the present invention pursuant to NHLBI Grant HL 17669.

BACKGROUND OF THE INVENTION

1. Field of the Invention

The present invention relates generally to methods and compositions for replacement gene therapy, and more particularly relates to adenovirus vectors adapted for delivering functional apolipoprotein A-I (apoA-I) genes to liver cells. It is proposed that the methods and compositions disclosed herein will be applicable to elevating the HDL (high density lipoprotein) form of cholesterol and thus suitable for use in treating atherosclerosis and reducing cardiovascular risk.

2. Description of the Related Art

Epidemiologic data demonstrate an inverse relationship between circulating levels of high density lipoprotein cholesterol (HDL cholesterol) and the incidence of clinically significant atherosclerosis (Miller, 1987; Manninen et al., 1988; Kottke et al., 1986; Gordon et al., 1989). This relationship holds for even small increments of HDL cholesterol, such that each 1 mg/dl increase in HDL cholesterol level is associated with a 2–3% decrement in cardiovascular risk (Gordon et al., 1989). Experimental evidence also supports a protective effect of HDL against atherosclerosis. Cholesterol-fed rabbits treated by infusion of purified homologous HDL are protected against the development of fatty plaques despite unchanged circulating HDL cholesterol levels (Badimon et al., 1989; Badimon et al., 1990; Badimon et al., 1992). This association between HDL cholesterol and the incidence of atherosclerotic vascular disease suggests that strategies to increase circulating HDL could have important clinical application. A modest increase in HDL cholesterol has been observed in patients treated with gemfibrozil (Badimon et al., 1989), an intervention associated with a reduced incidence of cardiac events. Trials intended to specifically assess the effects of intervention to increase HDL cholesterol on the development and progression of atherosclerosis are in progress (Goldbourt et al., 1993; Rubins et al., 1993).

HDL appears to exert its antiatherogenic effect by mediating reverse cholesterol transport, in which cholesterol is mobilized from peripheral tissues and transported to the liver (Eisenberg, 1984; Reichl et al., 1986; Miller, 1990). The small, high density, pre-beta subspecies of HDL, comprised predominantly of apolipoprotein A-1 and phospholipid is thought to act as the physiologic acceptor for cholesterol in the extracellular matrix of peripheral tissues (Reichl et al., 1986). Peripheral availability of this "scavenger" particle appears to be regulated by the rates of synthesis, secretion and catabolism of HDL (Eisenberg, 1984; Reichl et al., 1986; Miller, 1990).

Both clinical and experimental data suggest that the principal protein constituent of HDL, apolipoprotein A-1, mediates the antiatherogenic activity of HDL (Miller, 1987), and that the rate of production of apoA-I is a critical determinant of circulating HDL cholesterol. Families with both heritably deficient (Karathanasis et al., 1983; Vergani et al., 1981; Third et al., 1984; Ordovas et al., 1986) and enhanced (Glueck et al., 1976) apolipoprotein A-1 levels have been identified, and show corresponding alterations in HDL cholesterol. Persons with familial hyperalphalipoproteinemia appear protected from atherosclerosis, while those deficient in apolipoprotein A-1 show accelerated cardiovascular disease. Mice transgenic for a copy of the human apolipoprotein A-1 gene demonstrate accumulation of human apoA-1 in serum, increased circulating HDL cholesterol, and resistance to the atherogenic effects of a high cholesterol diet (Rubin et al., 1991; Walsh et al., 1989; Sorci-Thomas et al., 1988; Rubin et al., 1991). Thus, while the mechanisms regulating the rate of apolipoprotein A-1 synthesis are not clearly defined, genetic factors appear to exert an important effect (Widom et al., 1991).

A potential approach to increasing levels of apolipoprotein A-1 is somatic cell gene therapy. Recently, adenovirus-mediated gene transfer has been investigated as a means of mediating gene transfer into eukaryotic cells and into whole animals (van Doren et al., 1984a; van Doren et al., 1984b; Ghosh-Choudhury and Graham, 1987; Stratford-Perricaudet et at., 1990; Rosenfeld et al., 1991; Rosenfeld et al., 1992). Stratford-Perricaudet et al. (1990) have shown that adenovirus-mediated gene transfer can be used to treat a rare recessive genetic disorder, ornithine transcarbamylase (OTC) deficiency, in newborn mice. Unfortunately, the expression of the ornithine transcarbamylase enzyme in the virus injected mice was comparable to that in normal mice in only 4 out of 17 instances. In one out of 17 instances the level was about half the normal level, and in the remaining 12 out of 17, it was less than 20% of normal. Therefore, the defect was only partially corrected in most of the mice and led to no phenotypic or physiologic change in those mice.

Attempts to use adenovirus to transfer the gene for cystic fibrosis transmembrane conductance regulator (CFTR) into the pulmonary epithelium of cotton rats have also been successful, although it has not been possible to assess the biological activity of the transferred gene in the epithelium of the animals (Rosenfeld et al., 1992). Again, these studies demonstrated gene transfer and expression of the CFTR protein in lung airway cells but showed no physiologic effect. In the 1991 Science article, Rosenfeld et al. showed lung expression of $\alpha$1-antitrypsin protein but again showed no physiologic effect. In fact, they estimated that the levels of expression that they observed were only about 2% of the level required for protection of the lung in humans, i.e., far below that necessary for a physiologic effect. These results therefore do not demonstrate that adenovirus is able to transfer genes into cells and direct the expression of sufficient protein to achieve a physiologically relevant effect, and would not suggest a usefulness of the adenovirus system for use in connection with apo A-1 gene therapy.

Similarly, the gene for human $\alpha_1$-antitrypsin has been introduced into the liver of normal rats by intraportal injection, where it was expressed and resulted in the secretion of the introduced human protein into the plasma of these rats (Jaffe et al., 1992). However, the levels that were obtained were not high enough to be of therapeutic value.

In an alternate approach, a plasmid construct which encodes the human ApoA1 gene has been encapsulated in liposomes and introduced into the liver of rats by direct injection (Frolkis et al., 1991). This method resulted in increased HDL levels in the animals. However, the procedure is invasive, requiring anesthesia and an incision in the abdominal wall in order to introduce the liposome suspension directly into the liver.

Thus, there is clearly a significant need for novel therapeutic approaches that would be applicable to the treatment of diseases involving atherosclerosis. There is a particular need for the development of approaches that can lead to significant increases in HDLc. There is also a particular need for treatment methodologies that do not require surgical intervention, such as direct injection into the liver or modification of hepatocytes ex vivo.

SUMMARY OF THE INVENTION

The present invention addresses one or more of these or other shortcomings in the prior art through the provision of an adenovirus mediated technique for introducing human apoA-1 coding sequences into eukaryotic cells and expression and secretion in liver cells without the need for surgical intervention. The technique of the present invention circumvents many of the problems of the currently available techniques, and is based upon the discovery by the inventors that adenovirus vectors can selectively deliver apoA-1 coding sequences to liver cells and effect expression therein, and thereby achieve a physiologically significant effect.

In view of these observations, somatic cell gene transfer to augment apolipoprotein A-1 expression offers a new and potentially effective therapeutic approach. In an embodiment of the present invention, normal mice infected with a recombinant adenovirus encoding human apolipoprotein A-1 express high levels of human apoA-1 in serum. These animals demonstrate increases in circulating HDL cholesterol similar to those observed in mice transgenic for a copy of the human apolipoprotein A-1 gene, and of a magnitude previously associated with a protective effect against the development and/or progression of experimental atherosclerosis.

The invention generally relates to an adenovirus vector construct which includes a human apoA-1 expression region recombinant insert that is capable of expressing human apoA-1 in transformed cells. As used herein, a human apoA-1 expression region recombinant insert is defined as a DNA sequence that encodes the mature human apoA-1 protein, as, for example disclosed in Karathanasis et al., 1983 and Law and Brewer, 1984 joined to, 3' of and in frame with, the secretory signal sequence from human tissue plasminogen activator (tPA), for example. The expression region may also comprise a promoter and a polyadenylation site. In its most preferred embodiment, the vector is vector AdCMVapoA-1 as constructed by the methods disclosed hereinbelow in Example 6. While for ease of use one will prefer to employ a sequence derived from an apoA-1 cDNA sequence, it is contemplated that genomic sequences may be employed where desired.

The practice of the present invention rests in part upon the discovery that adenovirus vectors have been found by the inventors to selectively direct recombinant expression coding sequences to liver cells, and that these are efficiently expressed in the liver. The adenovirus vectors of the present invention have been rendered replication defective through deletion of the viral early region 1 (E1A) region such that the virus is competent to replicate only in cells, such as human 293 cells, which express adenovirus early region 1 genes from their cellular genome. This is important because the virus will therefore not kill normal cells because these cells do not express early gene products. Techniques for preparing replication defective adenoviruses are well known in the art as exemplified by Berkner et al., 1983, Ghosh-Choudhury et al., McGrory et al., 1988, and Gluzman et al.; see also U.S. Ser. No. 07/823,747, filed Jan. 22, 1992, incorporated herein by reference).

The examples of preferred embodiments disclosed herein utilize human adenovirus type 5. Type 5 virus was selected because a great deal of biochemical and genetic information about the virus is known, and it has historically been used for most constructions employing adenovirus as a vector. It is understood, however, the adenovirus may be of any of the 42 different known serotypes of subgroups A–F. Adenovirus type 5 of subgroup C is the preferred starting material in order to obtain the conditional replication-defective adenovirus vector for use in the method of the present invention.

Any of a large number of promoters may be used to direct expression the apoA-1 gene. In the examples given, the human cytomegalovirus (CMV) immediate early gene promoter has been used (Thomsen et al., 1984), which results in the constitutive, high-level expression of the foreign gene. However, the use of other viral or mammalian cellular promoters which are well-known in the art is also suitable to achieve expression of the apoA-1, provided that the levels of expression are sufficient to achieve a physiologic effect.

By employing a promoter with well-known properties, the level and pattern of expression of apoA-1 following infection can be optimized. For example, selection of a promoter which is active specifically in liver cells (such as the α1-antitrypsin, apolipoprotein A-1, liver fatty acid binding protein, LDL receptor, or plasminogen activator inhibitor type 1 (PAI-1) gene promoters) will permit tissue-specific expression of the apoA-1. Further, selection of a promoter that is regulated in response to specific physiologic signals can permit inducible expression of the apoA-1. For example, with a recombinant adenovirus in which the reporter coding sequence of β-galactosidase is expressed from the human PAI-1 promoter, Applicants have found that β-galactosidase expression can be induced in endothelial cells by tumor necrosis factor.

The secretory signal sequence to be used in the practice of the present invention may be any signal sequence that will direct the proper secretion of the apoA-1 protein. The human tissue plasminogen activator (tPA) secretory signal sequence was chosen because of the convenience of the location of restriction enzyme recognition sites that were compatible with the one in the propeptide cleavage site from human apolipoprotein A-1. It is understood that any signal sequence which can be joined to the apoA-1 gene in frame and which will direct the secretion and maturation of a propeptide from a mammalian cell in an efficient manner is acceptable; however, certain secretory signal sequences may have advantages under different conditions and one will select these depending on the particular circumstances. Alternative secretory signal sequences which may be used include, but are not limited to human PA1-1 or the endogenous apoA-1 sequences with the human tissue plasminogen activator signal sequence being the most preferred.

The vectors of the present invention are replication defective, and as such they will typically not have an adenovirus E1 region. Thus, it will be most convenient to introduce the apoA-1 coding region at the position from which the E1 coding sequences have been removed. However, the apoA-1 coding region may be inserted in other regions as long as it is expressed. The apoA-1 transcription unit may also be inserted, e.g., in the position of the deleted E3 region in E3 replacement vectors as described previously by Karlsson et at. (1986). Moreover, where a cDNA insert is employed one will typically desire to include a polyadenylation signal to effect proper polyadenylation of the apoA-1 message. Any such sequence may be employed. The inventors prefer to employ either the SV40 or protamine gene polyadenylation signal in that they are convenient and known to function well in the target cells employed.

In further embodiments, the invention relates to pharmaceutical compositions wherein the adenovirus vector/ apoA-1 gene construct is dispersed in a pharmacologically acceptable solution or buffer. Preferred solutions include neutral saline solutions buffered with phosphate, lactate, Tris, and the like. Of course, one will desire to purify the vector sufficiently to render it essentially free of undesirable contaminant, such as defective interfering adenovirus particles or endotoxins and other pyrogens such that it will not cause any untoward reactions in the individual receiving the vector construct. A preferred means of purifying the vector involves the use of buoyant density gradients, such as cesium chloride gradient centrifugation.

In still further embodiments, the invention relates to a method for increasing the plasma high density lipoprotein cholesterol in a subject comprising administering to the subject an effective amount of a pharmaceutical composition which includes the adenovirus vector/apoA-1 construct. Extrapolating from the data set forth hereinbelow, the inventors propose that an effective amount of the vector construct will involve the administration of from about $5 \times 10^{10}$ to $5 \times 10^{12}$ virus particles, which may be given either as a single bolus injection or as an intravenous infusion over several hours.

In that adenovirus is a virus that infects humans, there may be certain individuals that have developed antibodies to certain adenovirus proteins. In these circumstances, it is possible that such individuals might develop an immunological reaction to the virus. Thus, where an immunological reaction is believed to be a possibility, one may desire to first test the subject to determine the existence of antibodies. Such a test could be performed under a variety of accepted protocols, for example, through a simple skin test or through a test of the circulating blood levels of adenovirus-neutralizing antibodies. In fact, under such circumstances, one may desire to introduce a test dose of on the order of $1 \times 10^5$ to $1 \times 10^6$ or so virus particles. Then, if no untoward reaction is seen, the dose may be elevated over a period of time until the desired dosage is reached, such as through the administration of incremental dosages of approximately an order of magnitude.

It should also be pointed out that because the adenovirus vector employed is replication defective, it will not be capable of replicating in the cells that are ultimately infected. Moreover, it has been found that the genomic integration frequency of adenovirus is usually fairly low, typically on the order of about 1%. Thus, where continued treatment in certain individuals is required it may be necessary to reintroduce the virus every 6 months to a year. In circumstances where it may be necessary to conduct long term therapy, the individual's plasma cholesterol levels are monitored at selected intervals.

The particular cell line used to propagate the recombinant adenoviruses can be any cell which will support replication of the replication deficient virus, or any cell that can supply the E1 region function in trans. The recombinant adenovirus vectors can be propagated on, e.g., human 293 cells, or in other cell lines that are permissive for conditional replication-defective adenovirus infection, e.g., those which express adenovirus E1A gene products "in trans" so as to complement the defect in a conditional replication-defective vector. Further, the cells can be propagated either on plastic dishes or in suspension culture, in order to obtain virus stocks thereof.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 6A demonstrates the $^{125}$I-LDL clearance from plasma in mice injected with $8 \times 10^8$ pfu AdCMV-LDLR.

FIG. 6B demonstrates the $^{125}$I-LDL clearance from plasma in mice injected with $2 \times 10^9$ pfu AdCMV-LDLR.

FIG. 6C demonstrates the $^{125}$I-LDL clearance from plasma in mice injected with $2 \times 10^9$ pfu AdCMV-LDLR.

FIG. 6D demonstrates the $^{125}$I-LDL clearance from plasma in mice injected with $3.5 \times 10^9$ pfu AdCMV-LDLR.

FIG. 12 is the analysis of density purified lipoproteins in pooled serum from AdCMVapoA-I infected mice. Samples of serum obtained from mice 5 days after infection with AdCMVapoA-I were pooled and the lipoprotein containing fraction (ρ<1.21) isolated by KBr density gradient ultracentrifugation. Lipoproteins were further fractionated by chromatography on SUPEROSE 6, and fractions eluting from the column analyzed for protein, human apolipoprotein A-I, cholesterol and triglycerides. Human apoA-I co-eluted with the major cholesterol peak in a position corresponding to HDL. Cholesterol and triglyceride elution profiles for lipoprotein samples prepared from serum from uninfected and AdRR5-infected mice were qualitatively similar.

DETAILED DESCRIPTION OF THE PREFERRED EMBODIMENTS

Figure 1:
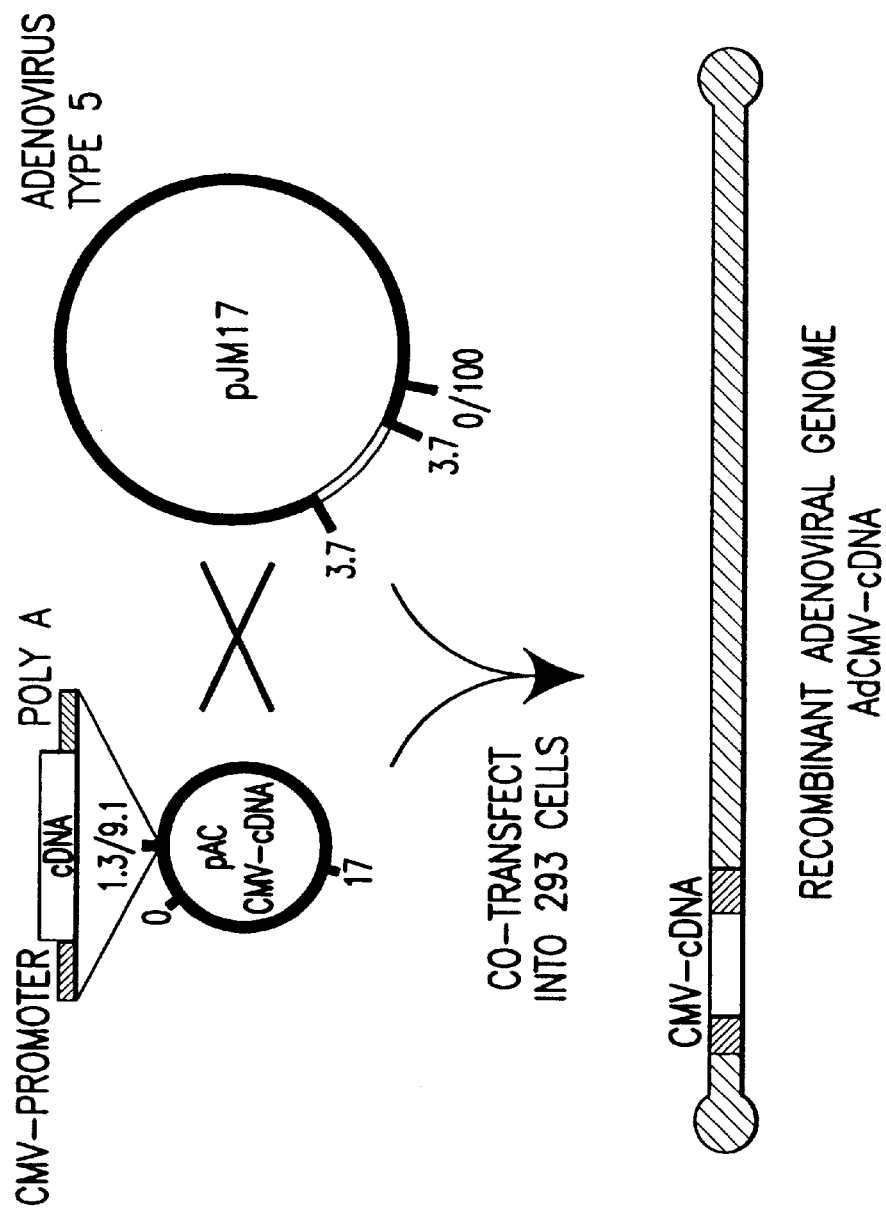
FIG. 1 is a schematic representation showing the construction strategy for preparing the recombinant adenoviruses employed in the studies set forth in Example I.

The present invention disclosure demonstrates that an animal infected with a recombinant adenovirus containing a gene encoding human apolipoprotein A-I may efficiently synthesize and secrete the human protein into serum. Protein expressed from the foreign gene is apparently incorporated into physiologic HDL particles, and infected animals demonstrate a significant increase in circulating HDL cholesterol levels. These observations imply that the rate of apoA-I synthesis and secretion from the liver is an important determinant of circulating HDL cholesterol. The increase in HDL cholesterol following adenovirus mediated gene transfer is similar to that in animals transgenic for a copy of the human apoA-I gene. The increase in HDL cholesterol in animals expressing the recombinant apoA-1 gene, moreover, is large relative to levels affording significant protection against the progression of atherosclerosis in both clinical and experimental studies (Miller, 1987; Manninen et al. 1988; Kottke et al. 1986; Gordon et al., 1989), and is large relative to increases associated with a reduction in cardiovascular risk in humans (Manninen et al. 1988).

Introduction of foreign genes into somatic cells in intact animals has been achieved with a variety of vectors, including recombinant retroviruses, synthetic vectors and recombinant adenoviruses (reviewed in Berkner, 1988; Miller, 1992; Anderson, 1992; Gerard et al., 1993), and in some cases expression of cellular proteins or paracrine growth factors has been sufficiently efficient to produce demonstrable physiologic effects. In vivo somatic cell gene transfer to produce physiologically meaningful quantities of a serum protein, however, has not been previously demonstrated. The embodiments of the present invention described herein demonstrate that adenovirus mediated gene transfer results in significant overexpression of a serum protein such as human apolipoprotein A-1.

The present invention also demonstrates the feasibility of using replication-defective adenovirus particles to transfer the LDL receptor gene into the liver, as a means of reducing plasma cholesterol levels. Following a single peripheral intravenous injection, a high proportion of hepatic parenchymal cells were infected with the recombinant virus and efficiently expressed foreign genes harbored within the adenovirus genome of the particular vector employed (β-galactosidase, firefly luciferase, human LDL receptor and apolipoprotein A-1). Importantly, expression of the human LDL receptor gene resulted in plasma cholesterol levels that were lower than those measured in animals that had been injected with a virus carrying the β-galactosidase gene. Likewise, clearance of $^{125}I$-labeled LDL from the circulation was significantly accelerated in mice injected with AdCMV-LDLR. This effect was dependent upon the number of pfu injected into the animals.

The amount of LDL receptor in the livers of animals injected with $2\times10^9$ pfu of AdCMV-LDLR was increased approximately 10-fold over that found in the livers of uninjected control mice. The inventors' results. demonstrate that adenovirus-mediated gene transfer provides strong transient expression of an exogenous LDL receptor gene in the livers of virus injected mice. The level of receptor expression that was achieved in the in vivo systems tested strongly suggests its potential use in the treatment of familial hypercholesterolemia (FH), a frequent human genetic disorder.

After peripheral intravenous injection a high percentage of the liver cells are targeted by recombinant adenovirus carrying the β-galactosidase gene. The liver is the primary organ targeted by adenovirus in mice as shown by the distribution of luciferase activity 4 days after intravenous administration of AdCMV-Luc. In addition to expression in parenchymal liver cells, the adenovirus-transferred genes were also expressed in endothelial cells lining the sinusoids and blood vessels as judged from expression of β-galactosidase in these cells also.

The inventors results are in contrast to the results reported by Jaffe et al. (1992). These authors reported that after intraportal injection of $10^{10}$ pfu of adenovirus carrying the β-galactosidase gene into rats only 1% of hepatocytes tested positive for β-galactosidase activity 3 days after virus administration. No infected hepatocytes were detected when the same amount of virus was injected into the tail vein. No β-galactosidase staining of endothelial cells was observed in either case. The recalcitrance of infection of hepatic endothelial cells in vivo is in contrast to other endothelial cells; for example the efficient adenovirus-mediated gene transfer to human umbilical cord endothelial cells ex vivo using the same recombinant viruses (Lemarchand et al. (1992)).

As shown in the studies set forth below, the CMV promoter is employed to drive expression of the inserted genes. However, it is contemplated that other promoters may be successfully employed where desired, such as the Rous sarcoma virus long terminal repeat (RSV-LTR) that was employed by Jaffe et al. (1992). One will prefer to employ a strong promoter such as the CMV promoter for the practice of the invention because a high expression level in the liver is important. In general, it is believed that any promoter may be employed, so long as it is sufficiently strong to promote a physiologic effect. Exemplary promoters include, for example, the SV40 early gene promoter, the RSV-1 LTR promoter, the β-actin promoter, the $α_1$-antitrypsin promoter, the PA1-1 promoter, the fatty acid binding protein promoter and the like. Use of the endogenous apolipoprotein AI promoter to drive expression exclusively in the hepatocytes is also contemplated.

It is believed that the expression of exogenous genes transferred in vivo by adenovirus can persist for extended periods of time. However, therapeutic protocols, particularly where long-term treatment is indicated, will likely be addressed on a case by case basis. Marker genes may be limited in their usefulness to assess therapeutically relevant persistence of gene expression because the expression levels required for the amelioration of any given genetic disorder may differ considerably from the level required to completely cure another disease. For example, it is expected that relatively high expression will be necessary to treat $α_1$-antitrypsin deficiency because the $α_1$-antitrypsin molecule is consumed in the reaction with its target protease, neutrophil elastase. Sufficiently high expression levels of this protein have not yet been obtained (Jaffe et al., 1992).

The inventors have demonstrated high level expression of recombinant human apolipoprotein A-1. The levels of apolipoprotein A-1, as shown in mice, fell to <10% of peak levels 12 days after infection. Such high expression is expected to have positive physiological benefits because augmentation of endogenous gene function resulting in low level increases in HDLc levels have been shown to have physiological benefits. In part, the decline in expression from the recombinant gene may reflect extinction of expression in mice from the human cytomegalovirus promoter used in these experiments (Scharfmann et al., 1991). Additionally, mice will probably develop antibodies to the human apoA-1 protein that will affect the steady state expression level of apoA-1 in plasma. The inventors have observed the development of antibodies to both adenovirus proteins and expressed foreign proteins following adenovirus mediated gene transfer in mice. One will therefore wish to make further determinations to ascertain the most efficient and stable expression system for each individual subject. However, such optimization is within the ability of those skilled in the art in light of the present disclosure.

Safety-related concerns of the use of replication deficient adenovirus as a gene transfer vehicle in humans have been addressed in the past (Rosenfeld et al., 1992; Jaffe et al., 1992). A transient lymphocytic infiltrate has been observed in the livers of experimental animals infected with high titers of recombinant adenovirus. Similar inflammatory responses were observed in animals infected with AdCMVapoA-I and control viruses, suggesting that this response is related to the vector rather than the inserted foreign gene. To assess whether administration of AdCMVapoA-1 to normal mice produced a lymphocytic hepatitis, liver tissue was harvested from animals 5, 12 and 26 days after infection for histologic examination. As anticipated from prior observations, a prominent lymphocytic infiltrate was observed in hepatic tissue 5 days after infection. Similar infiltrates were observed in liver tissue harvested from AdRR5 infected mice, suggesting a response to the viral vector rather than to the encoded foreign gene. By 12 days, the inflammatory response appeared significantly less, and 26 days after infection, no residual infiltrate was observed.

Despite the histopathologic abnormalities, serum γ-glutamyl transpeptidase and bilirubin levels were not increased in either AdCMVapoA-I or AdRR5 infected mice in comparison to uninfected control animals. A similar lymphocytic hepatitis has previously been observed in mice infected with a recombinant adenovirus encoding the human low density lipoprotein receptor (Herz et al., 1993), and inhalation of human adenovirus 5 has been reported to produce a transient lymphocytic interstitial pneumonitis in rodents in the absence of evidence of viral replication (Prince et al., 1993).

Reasons for the observed immune response have not been determined. The immune response may result entirely from the administered load of viral antigen, or merely reflect low level expression of endogenous adenovirus genes by infected cells.

In mice infected with AdCMVapoA-I, an increase in total cholesterol was observed of a magnitude greater than that accounted for by the observed increase in HDL cholesterol. In addition, mice infected with AdCMVapoA-I, but not with AdRR5 or AdCMVLuc, demonstrated an unanticipated and significant increase in serum triglyceride levels. On SUPER-OSE 6 chromatography, the increased triglycerides eluted in the VLDL fraction, suggesting an indirect effect of overexpression of human apoA-I on VLDL metabolism similar to that described by Frolkis et al. (1991). These observations contrast with those in mice transgenic for a copy of the human apoA-I gene, in which no significant increase in serum triglycerides was observed (Rubin et al., 1991; Walsh et al., 1989). Identification of the mechanisms responsible for these alterations in lipoprotein profiles will require an analysis of endogenous murine apolipoproteins and lipoprotein turnover studies. Such studies might provide insight into unrecognized mechanisms regulating lipoprotein metabolism.

For the first time, the inventors have shown that somatic cell gene transfer will augment circulating apolipoprotein levels, and specifically will increase circulating HDLc levels. While the alterations in lipoprotein levels declined over a period of days in the mouse model, the duration is sufficient to have a positive physiological effect. Importantly, the disclosed methods provide in vivo models of lipoprotein metabolism, alleviating for some purposes the need to generate transgenic animals. This approach is particularly useful in studies of altered lipoprotein metabolism in i) larger animals more amenable to studies of vascular biology, ii) species with endogenous lipoprotein profiles more closely resembling those in humans, and iii) species in which generation of transgenic animals is difficult or impractical.

The potent antiatherogenic effects of HDL make it an attractive target for therapeutic intervention to prevent or retard the progression of atherosclerosis. Both clinical and experimental studies suggest that even minor alterations in HDL cholesterol can exert an important antiatherogenic effect, and the degree of augmentation of HDL cholesterol observed in the present studies has been associated with a protective effect in both experimental animals and humans. The present invention makes possible further studies of adenovirus mediated transfer of a gene encoding apolipoprotein A-I, and its ability to convey protective effects against the development of vascular disease in well-characterized animal models, and will lead to therapeutic applications of a gene-based strategy to reduce cardiovascular risk.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

PREPARATION OF RECOMBINANT ADENOVIRUS-LDL RECEPTOR CONSTRUCTS

This example describes the use of recombinant replication defective adenoviruses in the preparation of virus constructs carrying several different functional cDNAs.

A. Preparation of Recombinant Adenovirus

Recombinant adenovirus (Gluzman et al., 1982) containing distinct cDNAs (AdCMV-cDNA) were prepared as outlined generally in FIG. 1. Individual cDNAs encoding the human LDL receptor (Yamamoto et al., 1984), E. coli β-galactosidase carrying the SV40 T antigen nuclear targeting signal (Bonnerot et al., 1987), and the firefly luciferase gene (deWet et al., 1987) were inserted into pACCMV (Gomez-Foix, et al., 1992) to create three distinct constructs. The resulting expression cassettes comprise the cytomegalovirus (CMV) promoter, the respective cDNA and a polyadenylation signal from either the SV40 virus or the mouse protamine gene, and are flanked by adenovirus type 5 sequences extending from map units 0 to 1.3 and 9.1 to 17, respectively. In these constructs, the E1 region of adenovirus is replaced by the foreign genes. The resulting plasmids were cotransfected into 293 cells together with a plasmid carrying the complete adenovirus type 5 genome (pJM17). Plasmid sequences conferring ampicillin and tetracycline resistance are inserted into the virus genome at map position 3.7. Due to the packaging limit of adenovirus, pJM17 cannot efficiently form plaques on its own. Homologous recombination between the pAC-cDNA plasmid and pJM17 within a transfected cell results in a viable virus that can be packaged and form plaques only on 293 cells.

In the studies set forth below, three distinct cDNAs were employed, encoding the human LDL receptor (Yamamoto et al., 1984), E. coli β—galactosidase carrying the SV40 nuclear targeting signal (Bonnerot et al., 1987), and firefly luciferase (deWet et al., 1987). Three recombinant replication defective adenoviruses were ultimately generated, as described below, and termed AdCMV-LDLR, AdCMV-βGal, and AdCMV-Luc, respectively. DNA restriction enzyme digests, ligations and transformations were performed as described in Sambrook et al. (1989). The structure of the recombinant viruses generated were verified by restriction enzyme digestion and Southern blotting.

In the preparation of recombinant adenovirus for the expression of the human LDL receptor (AdCMV-LDLR), the XbaI-SmaI fragment of pSP15 (Peacock et al., 1988) containing the complete coding sequence of the receptor (Yamamoto et al., 1984) was employed. This DNA segment was inserted into the pACCMVpLpA vector (Gomez-Foix et al., 1992), and the resulting plasmid was co-transfected, with pJM17 (McGrory et al., 1988), into human embryonic kidney 293 cells that express adenovirus E1A proteins (Graham et al., 1977).

Co-transfection was performed as follows: 293 cells were cultured in Dulbecco's modified Eagle's medium (DMEM, from GIBCO-BRL) containing 10% fetal calf serum (FCS, from Hyclone) in a humidified 5% $CO_2$ atmosphere. Confluent 10 cm dishes were split to three 6 cm dishes the day before calcium phosphate cotransfection of 4 μg pJM17, 4 μg pACCMV-LDLR, and 12 μg HeLa DNA as carrier. Six hours after addition of the DNA to the cells, a 15% glycerol shock was used to boost transfection efficiency and the cells were overlaid with 0.65% Noble agar in DMEM containing 2% FCS, 50 μg/ml penicillin G, 10 μg/ml streptomycin sulfate, and 0.25 μg/ml fungizone (GIBCO). Monolayers were incubated for approximately 10 days until the appearance of viral plaques.

These plaques were picked, suspended in DMEM containing 2% FCS, and used to infect a new monolayer of 293 cells. When greater than 90% of the cells showed infection, viral lysates were subjected to a freeze/thaw cycle and were designated as primary stocks. Recombinant virus with the correct structure was verified by preparation of viral DNA from productively-infected 293 cells, restriction analysis, and Southern blotting. Secondary stocks were subsequently generated by infecting 293 cells with primary virus stock at a multiplicity of infection of 0.01 and incubation until lysis.

Recombinant viruses expressing either a nuclear-localized β-galactosidase (AdCMV-βgal) or firefly luciferase (AdCMV-Luc) were constructed essentially as described for AdCMV-LDLR using appropriately constructed pAC plasmids. The β-galactosidase transcription unit (provided by Randall Moreadith, UT Southwestern) in pACCMV-βgal consists of the CMV promoter, the nuclear localization signal from SV40 T antigen fused to the amino-terminus of β-galactosidase (Bonnerot et al., 1987), and the mouse protamine polyadenylation signal. The luciferase transcription unit (provided by Stephen Johnston, UT Southwestern) in pACCMV-Luc is comprised of the CMV promoter, the luciferase cDNA from pJD207 (de Wet et al., 1987), and the SV40 t-antigen splicing/polyadenylation signals.

B. Large Scale Preparation of Recombinant Adenovirus

The large scale production of recombinant adenovirus was performed in 293 cells grown either in 15 cm culture dishes or in suspension using Joklik's calcium-free MEM (GIBCO) supplemented with 10% FCS. Infected cells were lysed 48 hours post-infection with Dulbecco's PBS (GIBCO) containing 1 mM $MgCl_2$ and 0.1% NP-40. Virus-containing extracts were centrifuged at 12,000×g for 10 minutes to remove debris before precipitation of the virus particles by addition of 0.5 vol 20% polyethylene glycol (PEG) 8000, 2.5 M NaCl and incubation on ice for 1 hour. Virus was collected by centrifugation at 12,000×g for 10 minutes, resuspended in isotonic saline (135 mM NaCl, 5 mM KCl, 1 mM $MgCl_2$, 10 mM Tris-HCl, pH 7.4), and dialyzed against the same buffer overnight before sterilization through a 0.22 μm filter.

Alternatively, PEG precipitated virus was resuspended in 50 mM Tris-HCl pH 7.8 containing CsCl (d=1.10 g/ml), layered over a step-gradient formed of 2 ml CsCl (d=1.40) and 3 ml of CsCl (d=1.30), and centrifuged 2 hours at 20,000 rpm at 10° C. in a Sorvall TH641 rotor. Virus was collected from the lower interface and dialyzed overnight at 4° C. versus isotonic saline. Equivalent results were obtained with both methods of virus preparation.

EXAMPLE 2

FUNCTIONAL EXPRESSION OF AdCMV-LDLR IN VITRO

This example describes the functional expression of the LDL receptor, and the other cDNA-encoded enzymes, in infected human 293 cells.

A. Protein Detection by Western Blotting

Figure 2:
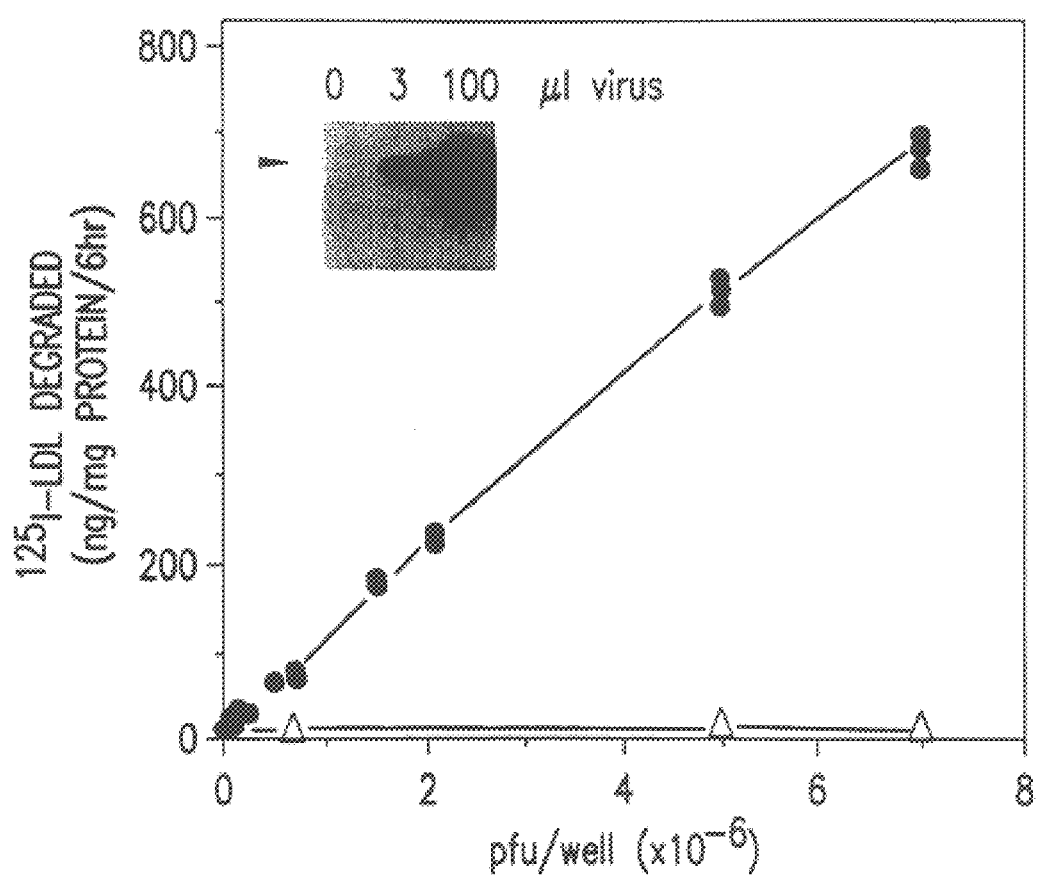
FIG. 2 is a bar graph showing the correlation between AdCMV-LDLR pfu and a dose dependent increase of $^{125}$I-LDL degradation in LDL-receptor defective CHO cells. The FIG. 2 inset is a western blot showing the increase in LDL receptors using an immunological detection method.

AdCMV-LDLR-infected 293 cells and mock-infected (control) cells were examined for the presence of the human LDL receptor protein by Western blotting with a mouse monoclonal antibody that specifically recognizes the human LDL receptor (Beisiegel et al., 1981). The endogenous LDL receptor present in the 293 cells was barely detectable by western blotting in this manner. However, infection of the cells with AdCMV-LDLR was found to lead to a dramatic increase in the amount of LDL receptor expressed 20 hours post infection (FIG. 2, insert). The total amount of human LDL receptor protein produced by 293 cells after infection with AdCMV-LDLR was dependent upon the amount of virus, i.e., 3 μl or 100 μl of primary virus stock, used to infect the cells (FIG. 2, insert).

B. Detection of Functional Protein by Activity Assay

The results presented above demonstrate the presence of the recombinant LDL receptor protein in the infected cells, but do not address its functional capacity. To quantify the activity of the LDL receptor produced by the AdCMV-LDLR construct, the ability of virally-infected cells to degrade $^{125}$I-labeled LDL was determined. The cells chosen to conduct these studies were the Chinese hamster ovary (CHO) cells, CHO ldlA7, that carry a defect in their endogenous LDL receptor gene (Krieger et at., 1981). These LDL-receptor defective cells provide an ideal background against which to measure virally-conferred LDL degradation.

The following methods were employed in these aspects of the present study: protein concentrations were determined by the method of Lowry et al. (1951); $^{125}$I-labeled LDL was prepared from human plasma LDL iodinated using the Iodomonochloride method (Goldstein et al., 1983a). The specific activities of $^{125}$-LDL preparations were 200 cpm/ng protein and 550 cpm/ng protein, respectively. CHO ldlA7 cells (Krieger et al., 1981) in 6-well dishes were infected with recombinant virus at densities of 6×10$^5$ and 1.7×10$^6$ cells/well, respectively, in 1 ml of DMEM containing 2% FCS. $^{125}$I-LDL (4 μg/ml) in DMEM without glutamine containing 0.2% bovine serum albumin was added to the cells 60 hours after infection and incubation was continued for 6 hours. The appearance of $^{125}$I-LDL degradation products in the medium was determined by measuring trichloroacetic acid-soluble radioactivity in the medium as described (Goldstein et al., 1983a).

In the studies depicted in FIG. 2, LDL-receptor defective CHO ldlA7 cells were infected with the indicated number of AdCMV-LDLR (closed circles) or AdCMV-βGal (open triangles) as described in the detailed examples. Degradation of $^{125}$I-LDL (4 μg/ml) was measured 60 hours post infection and normalized to the amount of protein present in each dish. The insert shows a Western blot of 293 cells with a monoclonal antibody directed against the human LDL receptor 20 hours after mock infection (0 μl) or infection with 3 μl or 100 μl of primary virus stock. Determinations were performed in triplicates and all individual data points were plotted. Some points are not resolved, as experimental variation was very small.

LDL-receptor defective CHO ldlA7 cells were infected with varying doses of AdCMV-LDLR or AdCMV-βGal (control), as described immediately above. The capacity of the infected cells to degrade $^{125}$I-LDL (4 μg/ml) was measured 60 hours post infection and normalized to the amount of protein present in each dish. It was found that the CHO ldlA7 cells infected with AdCMV-LDLR were able to degrade $^{125}$I-labeled LDL, whereas the addition of equivalent amounts of AdCMV-βGal virus did not enhance LDL degradation (FIG. 2). Furthermore, the amount of $^{125}$I-labeled LDL degradation by the AdCMV-LDLR-infected cells was found to increase in a linear fashion with the number of plaque forming units (pfu) of AdCMV-LDLR that had been added to the culture dish (FIG. 2).

EXAMPLE 3

TISSUE DISTRIBUTION OF ADENOVIRUS CONSTRUCTS IN VIVO

This example describes the tissue distribution of recombinant genes, exemplified by the marker gene, firefly luciferase, following adenovirus-mediated gene transfer in vivo.

Mice used throughout all the present studies were either purchased from Harlan (Balb/c, C57B1/6) or bred in house (outbred animals) and fed ad libitum throughout the course of the experiments. Prior to virus injections and turn-over studies animals were anesthetized by intraperitoneal Nembutal injection (100 μg/g body weight). The external jugular vein was exposed to view by a skin incision and the indicated virus or $^{125}$I-labeled LDL were injected in a total volume of 250 μl. The wound was closed by stapling.

To quantify the efficiency of adenovirus-mediated gene transfer to different tissues in vivo, the expression of firefly luciferase in various tissues was examined following intravenous administration of the AdCMV-Luc construct to experimental animals. The luciferase assay was conducted by excising tissue samples into 1 ml extraction buffer (70 mM potassium phosphate, 55 mM Tris-HCl, 2 mM $MgCl_2$, 0.7 mM DTT, pH 7.8 containing 250 μg/ml soybean trypsin inhibitor and 20 μg/ml aprotinin) on ice and homogenizing in a Brinkmann polytron. Extracts were microfuged for 5 minutes at 4° C. and aliquots of the supernatant were assayed immediately for luciferase activity (de Wet et al., 1987). A 50 μl sample of extract was added to 250 μl of assay buffer containing 43.2 mM glycyl-glycine pH 7.8, 22 mM $MgSO_4$, 2.4 mM EDTA, 7.4 mM ATP, 1 mM DTT and 0.4 mg/ml bovine serum albumin in a test tube which was placed into a Berthold Biolumat luminometer set at 25° C. The reaction was initiated by the injection of 100 μl of 0.13 mg/ml luciferin and integration of the light emission over 10 sec was measured.

Five outbred hybrid male mice were injected with $\sim 2 > 10^9$ pfu AdCMV-Luc into the external jugular vein. Luciferase activity in homogenates of the individual organs was determined 4 days after injection of the virus. Activities are expressed as luminometer units per total organ with the exception of muscle where activity is expressed on a per gram basis. Note that enzymatic activity is expressed on a logarithmic scale. The lower detection limit in this experiment was approximately $2 \times 10^3$ units.

Figure 3:
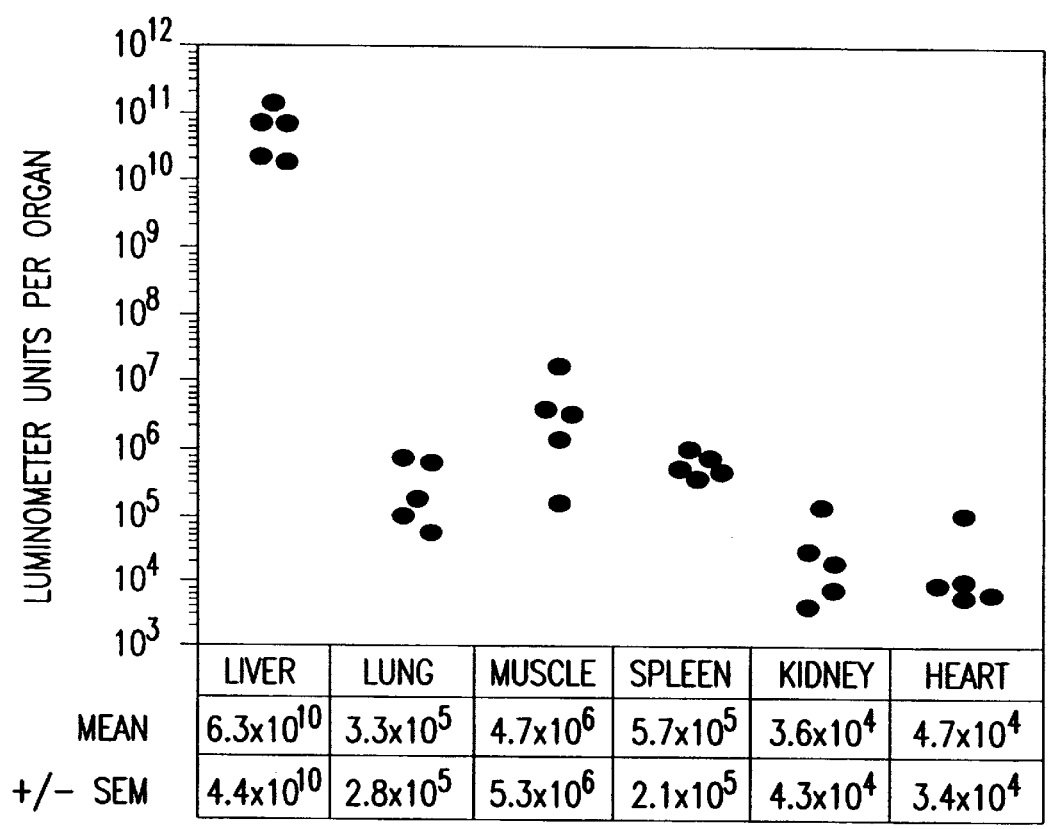
FIG. 3 shows the tissue distribution of luciferase activity in AdCMV-Luc injected animals, and further demonstrates the preferential targeting of adenovirus to the liver.

The luciferase activity in individual tissues was determined as described above. Low level luciferase activity was detected in all of the tissues examined including skeletal muscle and heart (FIG. 3). These organs had been shown to be target tissues for intravenously injected recombinant adenovirus (Stratford-Perricaudet et al., 1992). However, and particularly importantly, in this study more than 99% of the total enzyme activity recovered from the injected mice was found in the liver. No luciferase activity was expressed in uninjected animals which had uniform background levels regardless of the tissue examined.

EXAMPLE 4

SPECIFIC LDL RECEPTOR EXPRESSION IN VIVO

This example describes the expression of the LDL receptor in the liver following adenovirus-mediated gene transfer in vivo.

The results from the tissue distribution studies employing recombinant luciferase demonstrated the preferential targeting of the adenovirus construct to the liver. The following studies were designed in order to confirm that the recombinant virus was efficient in increasing the LDL receptors within the liver, the primary site of lipoprotein catabolism (Goldstein and Brown, 1989). Both western blotting studies and immunohistochemical analyses of the liver membranes were performed.

A. Western Blotting

Six female C57B1/6 mice (12 weeks old) were either not injected (FIG. 4, lanes 1–3) or injected (lanes 4–6) with $2 \times 10^9$ pfu of AdCMV-LDLR. 4 days after the injection the animals were sacrificed and liver membranes from each animal were subjected to Western blotting (250 μg protein/lane). The migration of the LDL receptor (LDLR) is indicated by the arrow. Total radioactivity present in each band was quantified by scanning the blot for 4 hours on an AMBIS Radioanalytic Imaging System. Background (~200 counts for each sample) was measured in a representative area of the blot and subtracted from the total counts to give the values shown. Liver LDL receptor concentrations were approximately 10 times higher in the LDLR virus injected mice than in the non-injected controls. Plasma cholesterol concentrations of the individual animals are expressed in mg/dl and are approximately 50% lower in the injected animals.

Mouse liver membranes (from both control and treated mice) were prepared by polytron-homogenization of a whole mouse liver in 20 ml of Homogenization Buffer, 10 mM Tris-HCl, 140 mM NaCl, pH 7.5, containing 1 mM PMSF (phenylmethylsulfonylfluoride), in a 50 ml Falcon tube. The homogenate was centrifuged for 10 minutes at 1000×g in a table-top centrifuge. The supernatant was then transferred to a new tube and centrifuged for a further 10 minutes at 10,000×g. 12 ml of the supernatant were harvested and 1 ml was subjected to ultracentrifugation at 200,000×g for 1 hour in a Beckman TL100 centrifuge. The supernatant was discarded and the pellet was resuspended in 200 μl Homogenization Buffer containing 1% Triton X-100.

Equal amounts of protein (250 μg) were mixed with 2×SDS (sodium dodecyl sulphate) sample buffer and electrophoresed on a non-reducing 6% SDS-polyacrylamide gel (SDS-PAGE). Proteins were electrotransferred to nitrocellulose membranes (Hybond, Amersham) as described by Towbin et al. (1979) and the presence of LDL receptors was determined by Western blotting.

In the Western blotting procedure, a rabbit polyclonal antibody was employed (10 μg/ml), in conjunction with $10^6$ cpm/ml $^{125}$I-labeled goat anti-rabbit IgG (Herz et al., 1992). The rabbit polyclonal antibody used has approximately equal reactivity against the human and mouse LDL receptors.

Figure 4:
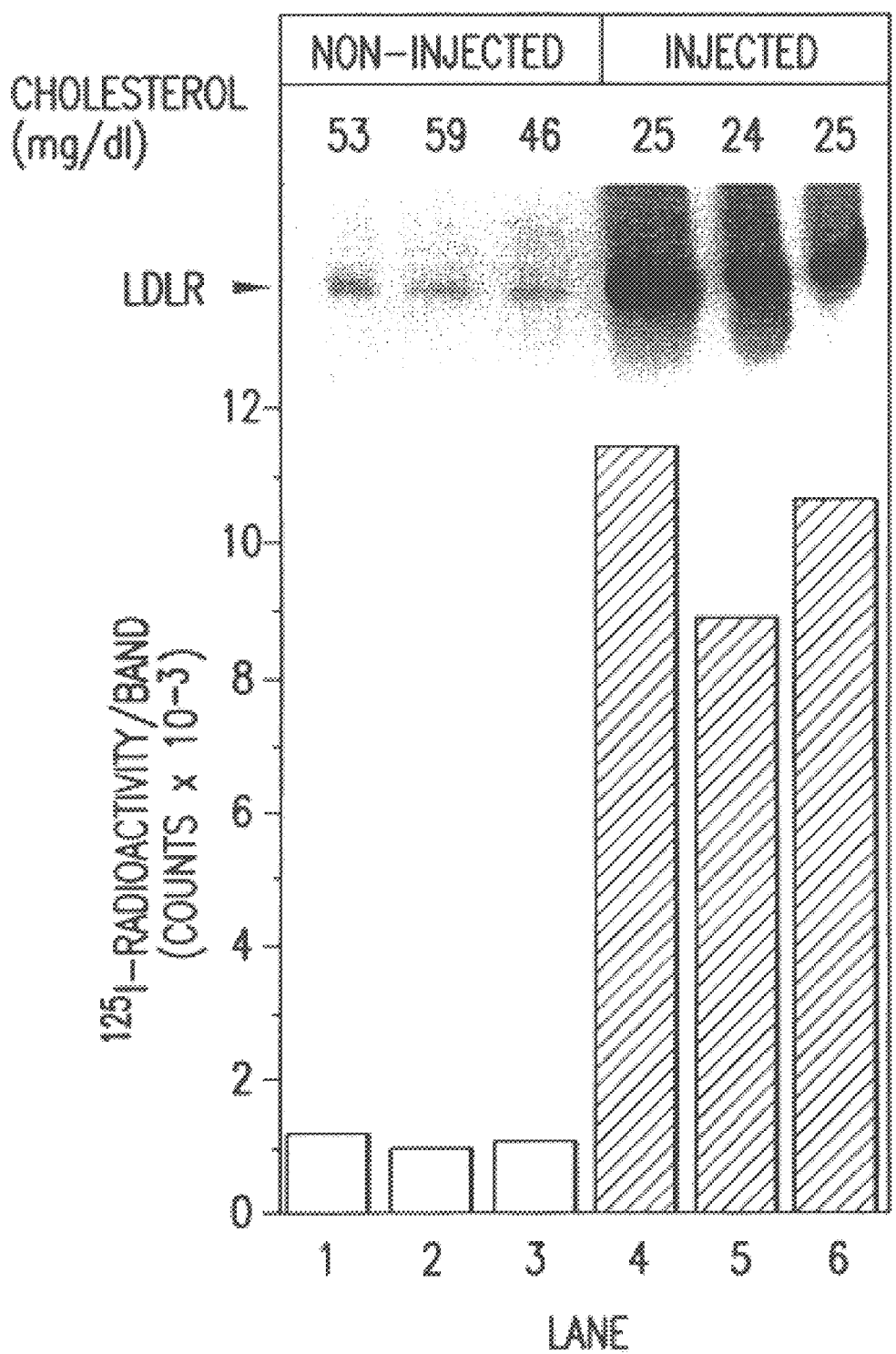
FIG. 4 is a bar graph showing that the intravenous injection of AdCMV-LDLR leads to LDL receptor overexpression in the liver. The inset is a Western blot showing the selective expression of immunologically reactive LDL receptor in the virally infected animals.

The results from these studies were tabulated, and are shown in FIG. 4. These results showed that the expression of LDL receptors in the livers of virus-injected animals was increased approximately 10-fold over that observed in the uninjected mice, and that expression was significantly enhanced in the liver over other tissues.

B. Immunofluorescence and Immunohistochemical Analyses

The expression pattern of the virally transferred genes for human LDL receptor and E. coli β-galactosidase in the livers of injected mice was next determined. For this purpose, liver sections of animals that had been injected with either $3.5 \times 10^9$ or $2 \times 10^9$ pfu of AdCMV-LDLR, or with $2 \times 10^9$ pfu of AdCMV-βGal, were examined for the presence of these enzymes. The LDL receptor was detected by immunofluorescence analysis using either polyclonal rabbit antibodies, or a mouse monoclonal specific for the human receptor, as primary antibodies.

Figure 5A:
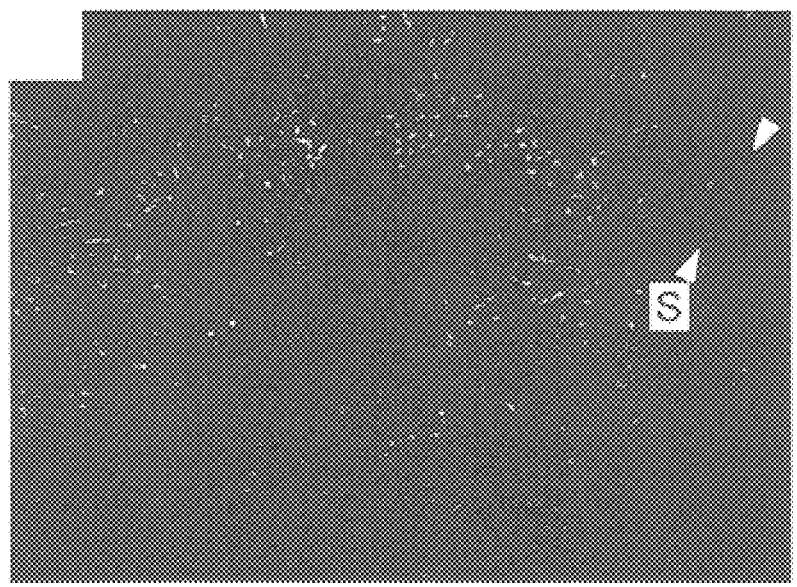
FIG. 5A shows the immunohistochemical analysis of human LDL receptor expression and histochemical detection of β-galactosidase activity in the liver of mice injected with $3.5 \times 10^9$ pfu AdCMV-LDLR detected with polyclonal rabbit IgG.
Figure 5B:
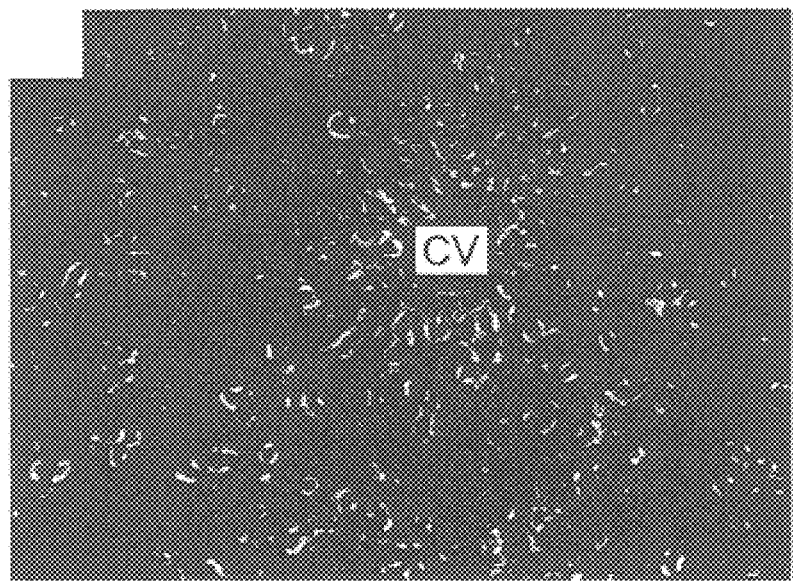
FIG. 5B shows the immunohistochemical analysis of human LDL receptor expression and histochemical detection of β-galactosidase activity in the liver of mice injected with $2 \times 10^9$ pfu AdCMV-LDLR detected with polyclonal rabbit IgG.
Figure 5C:
FIG. 5C shows the immunohistochemical analysis of human LDL receptor expression and histochemical detection of β-galactosidase activity in the liver of mice injected with $2 \times 10^9$ pfu AdCMV-βGal detected with polyclonal rabbit IgG.
Figure 5D:
FIG. 5D shows the immunohistochemical analysis of human LDL receptor expression and histochemical detection of β-galactosidase activity in the liver of mice injected with $3.5 \times 10^9$ pfu AdCMV-LDLR detected with a mouse monoclonal IgG that reacts specifically with the human receptor.
Figure 5E:
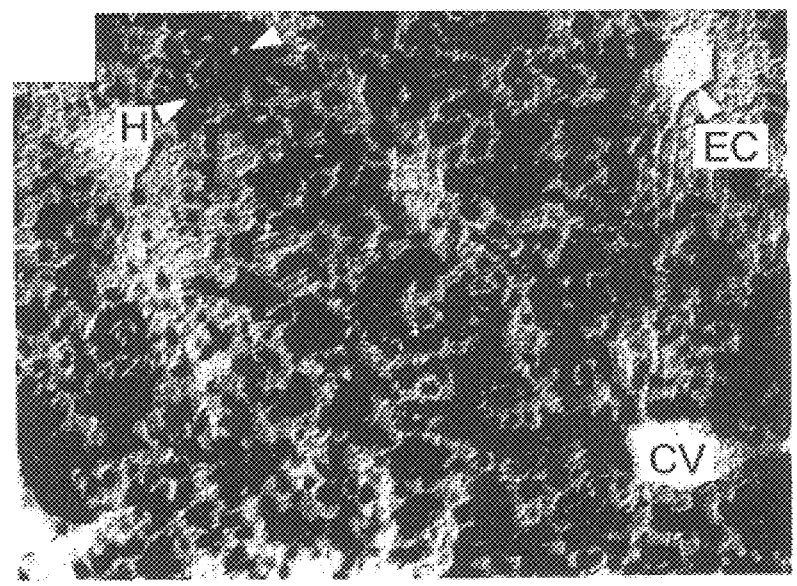
FIG. 5E shows the expression of β-galactosidase activity in the liver of mice injected with $2 \times 10^9$ pfu AdCMV-βGal.
Figure 5F:
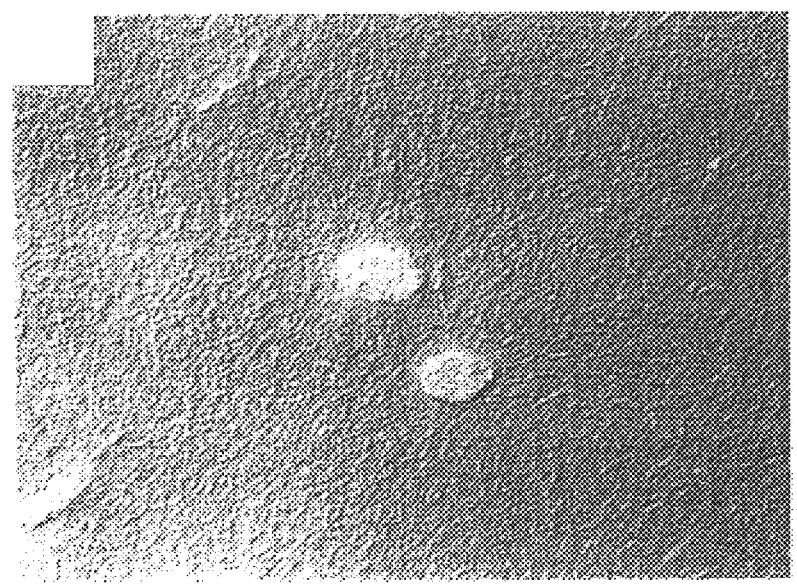
FIG. 5F shows the lack of β-galactosidase activity in the liver of mice injected with $3.5 \times 10^9$ pfu AdCMV-LDLR.

In the studies shown in FIGS. 5A–F, β-galactosidase activity was detected by immunohistochemical staining. Female Balb/c mice (~12 weeks) were injected with either $3.5 \times 10^9$ pfu (FIGS. 5A, 5D and 5F) or $2 \times 10^9$ pfu (FIG. 5B) AdCMV-LDLR or with $2 \times 10^9$ pfu AdCMV-βGal (FIGS. 5C and 5E). Expression of LDL receptor in the livers of the animals was detected with either a polyclonal rabbit IgG (FIGS. 5A–5C) or a mouse monoclonal IgG that reacts specifically with the human receptor (FIG. 5D). Specific staining is only present in the livers of animals injected with AdCMV-LDLR and absent in the AdCMV-βGal injected mouse. Up to an estimated 90% of the liver cells are expressing human LDL receptor which shows the typical polarized expression pattern (Yokode et al., 1992). Sinusoids (S, FIGS. 5A and 5C) that have been sectioned along their longitudinal axis are indicated by arrows. Expression of β-galactosidase activity (FIG. 5E) is found predominantly in the nuclei of hepatocytes (H) that are arranged in a typical columnar array (indicated by arrows in FIG. 5E). Nuclei of endothelial cells (EC) are stained less intensely. No β-galactosidase activity is found in mice injected with AdCMV-LDLR (FIG. 5F). CV, central vein. Magnification 37.5×.

For these analyses, the right lobe was removed from the livers of animals killed 4 days after injection of recombinant virus and a sector extending from the surface of the liver to the portal area was immediately frozen without fixation in OCT compound (Miles, Inc.) at −196° C. and stored at −70° C. until cutting. Sections of 6 μm, and 12 μm, for β-galactosidase staining, were cut on a Leitz Cryostat at −20° C. and mounted onto polylysine coated slides. Slides were stored at −20° C. until use.

Prior to immunostaining, tissue sections were fixed in 100% methanol at −20° C. for 30 seconds followed by 2 washes in phosphate buffered saline (PBS). All incubations were performed at 20° C. Sample were blocked by incubation in Buffer A (50 mM Tris-HCl, 80 mM NaCl, 2 mM $CaCl_2$, pH 8) containing 10% (v/v) normal bovine serum for 20 minutes. Sections were then incubated for 1 hour with the indicated concentrations of primary polyclonal or monoclonal IgG's followed by 3×5 minute washes in Buffer A. Bound primary antibody was detected by incubation with the indicated concentrations of fluorescein or rhodamine labeled secondary IgG's for 1 hour. Slides were then washed again three times in Buffer A, rinsed once briefly in water and mounted under a coverslip with DABCO (90% [v/v] glycerol, 50 mM Tris-HCl at pH 9, 25% [w/v]1,4-diazadicyclo-[2.2.2]-octane). Immunofluorescence of the sections was photographed using Ektachrome 800/1600 slide film on an Olympus IMT-2 microscope using the narrow band excitation filter packages supplied by the manufacturer.

For β-galactosidase staining, frozen sections were fixed at room temperature in 0.5% glutaraldehyde freshly prepared in PBS for 15 minutes and extensively washed in PBS. β-Galactosidase activity was detected by immersing the sections into X-Gal staining solution (35 mM $K_4Fe(CN)_6$, 35 mM $K_3Fe(CN)_{6,}$ 1 mM $MgCl_2$ and 1 mg/ml 5-bromo-4-chloro-3-indolyl-β-D-galactopyranoside (X-Gal, from GIBCO-BRL)) for 15 hours at 37° C. Sections were lightly counterstained with eosin prior to photography on an Olympus IMT-2 microscope and Ektachrome 160T film.

The results from these studies demonstrated that, as with the cultured cells, LDL receptor expression in vivo was dependent upon the injected amount of recombinant virus. While the highest amount of virus used ($3.5 \times 10^9$ pfu) resulted in a virtually uniform expression of LDL receptor in approximately 90% of the liver cells (FIG. 5A), $2 \times 10^9$ pfu of AdCMV-LDLR led to increased LDL receptor expression in roughly one half of the liver cells (FIG. 5B) as judged by immunofluorescence staining with a polyclonal anti-LDL receptor rabbit IgG. Although this antibody readily and specifically cross-reacts with the mouse receptor (Herz et al., 1992), expression of endogenous mouse LDL receptor was too low to be detected in liver sections from animals that had been injected with the virus carrying the β-galactosidase gene (FIG. 5C). Therefore, the increased LDL receptor expression in the AdCMV-LDLR injected mice was due to virally transferred human receptor and not due to increased transcription from the endogenous mouse gene.

A monoclonal mouse IgG that specifically recognizes only the human and the bovine LDL receptor showed a staining pattern that was virtually identical to the pattern observed with the polyclonal IgG (FIG. 5D). As was the case for the polyclonal IgG (FIG. 5C), no staining was observed in the livers of the AdCMV-βGal injected mice with this monoclonal antibody. Staining was also absent from kidney and heart, while isolated immunoreactive cells were observed in the lung. This is in agreement with the low levels of luciferase activity recovered from these organs 4 days after AdCMV-Luc injection (FIG. 3).

A similarly high percentage of liver cells of animals that had been injected with the adenovirus construct carrying the β-galactosidase gene were reactive upon histochemical examination for this enzyme (FIG. 5E), while β-galactosidase activity was completely absent from the livers of mice injected with AdCMV-LDLR (FIG. 5F). β-galactosidase activity was found not only in hepatocytes but also in a substantial fraction of the endothelial cells (EC, FIG. 5E) lining the blood vessels and the sinusoids. The degree of staining observed in the nuclei of the endothelial cells was not as intense as that seen in the majority of the parenchymal cells. Parenchymal hepatocytes are seen in a typical columnar array ('H', indicated by the arrows in FIG. 5E) when the plane of the section follows the longitudinal axis of the sinusoid.

The high percentage of liver cells that had been targeted by the injected virus and the homogeneously high level of expression is reflected in the 10-fold increase in the amount of LDL receptor present in the liver membranes of AdCMV-LDLR injected mice versus non-injected animals (FIG. 4).

EXAMPLE 5

FUNCTION OF RECOMBINANT LDL RECEPTORS IN VIVO

This example describes the functional activity of the LDL receptors expressed in the liver following adenovirus-mediated gene transfer in vivo.

The following studies were designed in order to assess whether the increased levels of the LDL receptor brought about by the adenovirus-mediated gene transfer were causing a physiologically relevant increase in receptor activity.

A. Cholesterol Levels

The cholesterol levels of virus-treated and control mice were determined, using the cholesterol oxidase method (Boehringer Mannheim). It was found that animals injected with $2 \times 10^9$ pfu of AdCMV-LDLR had significantly lower plasma cholesterol levels than non-injected controls (FIG. 4). The plasma cholesterol concentrations of the individual animals were found to be approximately 50% lower in the injected animals. This indicates that, not only was the LDL receptor cDNA contained in the virus transcribed and translated into immunologically-recognizable protein, but that the recombinant LDL receptors in the livers of these mice were also biologically functional.

B. $^{125}$I-LDL Turnover

The adenovirus-mediated transfer of the human LDL receptor gene in mice leads to the high level expression of the human receptor in the liver, the levels of which greatly exceed the expression of the endogenous murine receptor.

As the liver is the primary site of lipoprotein catabolism (Goldstein and Brown, 1989), the effects of viral gene transfer on LDL metabolism and cholesterol levels were determined.

To further quantitate the effect of the virus-mediated transfer of the exogenous LDL receptor cDNA, the rate of $^{125}$I-LDL turnover and steady state cholesterol levels in animals injected with AdCMV-LDLR, versus mice that had received the βGal-virus, was examined. In these studies, female Balb/c mice (~12 weeks) were injected with the indicated amount of AdCMV-LDLR or with a fixed amount of AdCMV-βGal (2×10$^9$ pfu). Four days after virus administration animals were injected with 15 μg $^{125}$I-LDL. Blood samples were analyzed at the indicated times as described in the detailed examples and the radioactivity remaining in plasma was plotted as a percentage of the activity present at 3 minutes after injection of the labeled ligand. Four separate experiments were performed. Individual clearance curves for each animal are shown. Steady state plasma cholesterol levels (in mg/dl) of each animal are indicated next to the last time point of the clearance curve. The mouse denoted by an asterisk in FIG. 6C showed shock symptoms during the clearance experiment and died shortly after the last time point was taken. This animal ceased to clear $^{125}$-LDL between 40 and 90 minutes. Hepatic circulation was presumably shut down as a result of circulatory shock.

FIGS. 6A–D show the results of 4 separate clearance studies performed with two different virus preparations. The $^{125}$I-labeled LDL was removed from plasma slowly by the control animals injected with AdCMV-βGal and the clearance rate ($t_{1/2}$>5 hours) was indistinguishable from that previously observed in normal mice (Hofmann et al., 1988). In contrast, AdCMV-LDLR significantly accelerated the removal of the radiolabeled ligand from the circulation of the animals. As a rule, the animals that cleared the $^{125}$I-labeled ligand most efficiently also had the lowest steady state plasma cholesterol levels four days after virus administration (FIGS. 6A–D and Table 1).

The rate of $^{125}$I-LDL clearance was dose dependent and proportional to the amount of pfu of AdCMV-LDLR that had been injected into the mice and was up to 10-fold greater than the rate observed in either normal (Hofmann et al., 1988) or AdCMV-βGal injected animals (this study).

The liver was the only organ in AdCMV-LDLR injected mice that showed a significant increase in $^{125}$I-LDL radioactivity versus control animals when the absolute tissue uptake of the labeled ligand was measured 20 minutes after injection (Table 1). Up to 45% of the injected dose was recovered in the livers of the LDLR-virus injected mice compared to ~13–15% that had accumulated in the controls. The tissue distribution of LDL receptor activity is therefore in agreement with the results obtained for AdCMV-Luc (FIG. 3), confirming that the liver is the primary target after peripheral intravenous injection of recombinant adenovirus.

TABLE 1

Tissue Uptake of $^{125}$I-LDL 20 min after Injection (% of injected dose)

| LDLR | + | + | + | | | |
|---|---|---|---|---|---|---|
| β-Gal | | | | + | + | + |
| Liver | 44.6 | 44.4 | 21.9 | 12.9 | 15.2 | 14.7 |
| Kidney | 1.1 | 2.2 | 2.5 | 2.2 | 3.4 | 2.9 |
| Lung | 0.9 | 1.4 | 1.8 | 1.7 | 1.7 | 1.4 |
| Spleen | 0.5 | 0.6 | 0.7 | 1.1 | 1.2 | 1.1 |
| Heart | 0.3 | 0.7 | 0.7 | 1.2 | 1.0 | 0.9 |

TABLE 1-continued

Tissue Uptake of $^{125}$I-LDL 20 min after Injection (% of injected dose)

| Plasma-Chol. (mg/dl) | 42 | 63 | 84 | 81 | 102 | 86 |
|---|---|---|---|---|---|---|

Female Balb/c mice (12 weeks) were injected either with 2×10$^9$ pfu AdCMV-LDLR or the same amount of AdCMV-βGal. Four days after virus administration the animals were injected with 7.5 μg $^{125}$I-LDL and killed 20 min later. Organs were removed, homogenized in phosphate buffered saline and radioactivity was determined in a sample of the homogenate. Total radioactivity recovered from the individual organs is shown as a percentage of the injected dose (4×10$^6$ dpm). Plasma cholesterol levels of the individual animals are shown in the last line.

EXAMPLE 6

PREPARATION OF RECOMBINANT ADENOVIRUS

This example describes the preparation of recombinant adenovirus containing the human apolipoprotein A-1 gene under the control of the CMV promoter substituted in the E-1 region of the adenovirus genome.

1. Generation of Recombinant Adenoviruses

Figure 7:
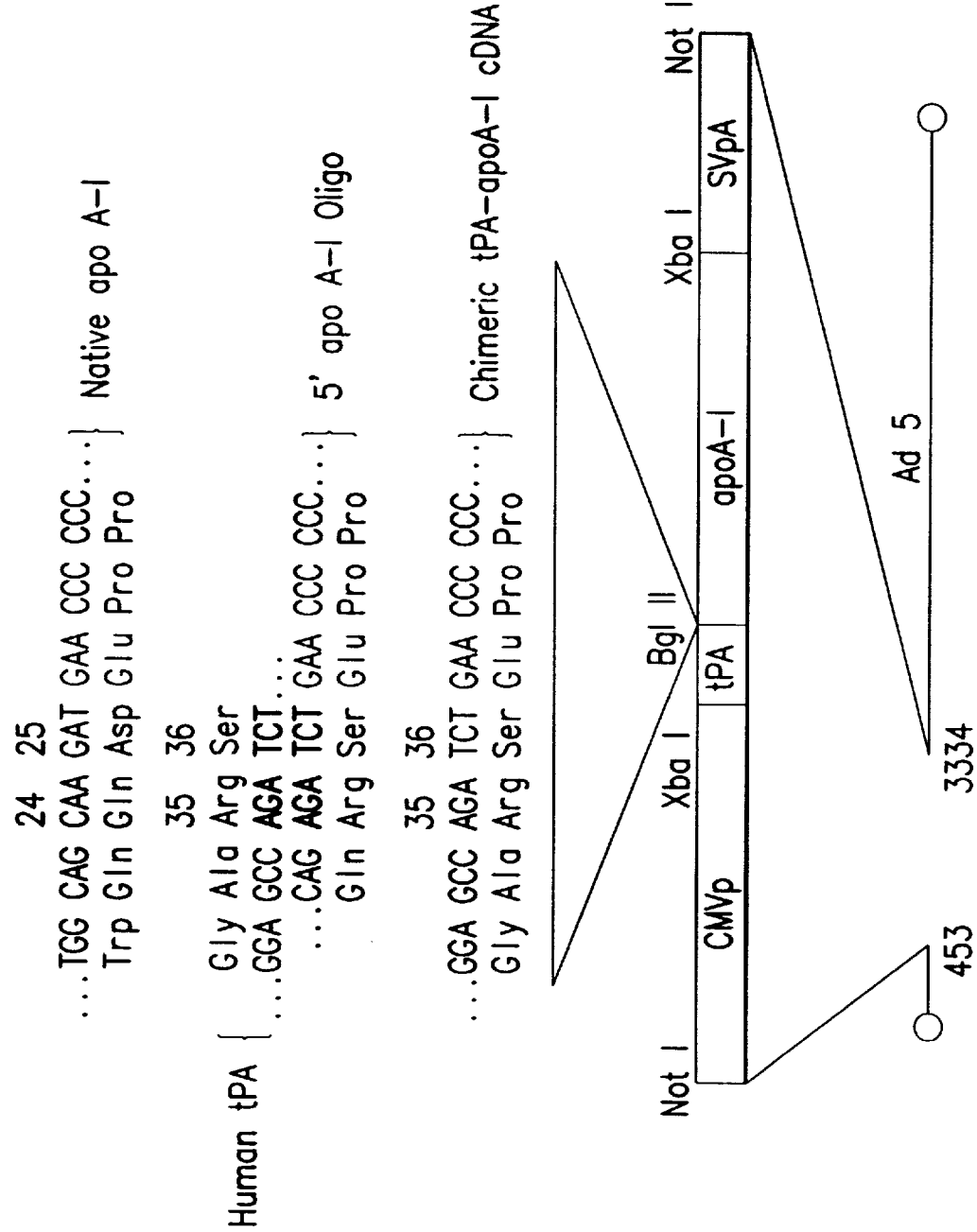
FIG. 7 is a schematic diagram of the construction of AdCMVapoA-I. A fragment of the cDNA encoding human tissue plasminogen activator and a partial cDNA encoding the mature human apolipoprotein A-I protein were ligated in frame using an artificial Bglll site (shown in bold type) introduced into the apoA-I sequence during amplification. The resulting chimeric cDNA encodes the mature form of apoA-I behind the secretory signal sequence of human tPA (residue numbers as shown). This cDNA was inserted into pACCMVpLpA between the human cytomegalovirus immediate-early promoter and transcriptional termination and polyadenylation sequences derived from SV40 to form a complete transcriptional unit. The recombinant adenovirus AdCMVapoA-I was generated by homologous recombination between pACCMVapoA-I and pJM17 after transfection into 293 cells. The sequences in this figures are represented, reading from the top to the bottom, by SEQ ID NO:3 through SEQ ID NO:10. In particular, the nucleic acid sequence from native apo A-1 is SEQ ID NO:3 and the amino acid sequence is SEQ ID NO:4. The amino acid sequence from human tPA is SEQ ID NO:5, and the nucleic acid sequence is SEQ ID NO:6. The nucleic acid sequence from 5' apo A-1 oligo is SEQ ID NO:7 and the amino acid sequence is SEQ ID NO:8. The nucleic acid sequence from chimeric tPA-apoA-1 cDNA is SEQ ID NO:9 and the amino acid sequence is SEQ ID NO:10.

The recombinant adenovirus AdCMVapoA-1 was generated by the strategy illustrated schematically in FIG. 7. Manipulation of recombinant DNA was performed essentially as described by Sambrook et al. (1989). Enzymatic reactions were performed under conditions recommended by the suppliers. A cDNA encoding mature human apolipoprotein A-1 was obtained by polymerase chain reaction from a human liver cDNA library (obtainable from Dr. David Russell, University of Texas Southwestern Medical Center, Dallas Tex.) using the oligonucleotide primers:

5' CGGCATTTCTGGCAGA GATCT GAACCCCCCCAGA3' (SEQ ID NO:1) and

5'TTTTCTAGA GCCTCACTGGGTGTTGAGCTTCTT3' (SEQ ID NO:2)

The underlined sequences correspond to positions (relative to the translational start) +55 to +89 and +764 to +788 in the previously reported human apolipoprotein A-1 cDNA (Karathanasis et al., 1983; Law et al., 1984). Sequencing of the cloned amplification product demonstrated agreement with the published sequence.

A cDNA fragment encoding the secretory signal peptide from human tissue plasminogen activator was obtained by digestion of the plasmid pST$_7$tPA (Madison et al., 1989) with Xbal and Bglll. The amplified partial apoA-1 cDNA was digested with Bglll/Xbal, and both fragments ligated into Xbal cut pACCMVpLpA (Gomez-Foix et al., 1992) to produce pACCMVapoA-1. This resulted in an in-frame fusion of sequences encoding the human tPA secretory signal sequence with sequences encoding mature human apolipoprotein A-I. In the resulting fusion protein, the Gln-Asp propeptide cleavage site in native human apolipoprotein A1 is replaced by the Arg-Ser site from human tPA, introducing an Asp to Ser substitution at the amino terminus of the mature apoA-1 protein. In the plasmid pACCMVapoA-1, this chimeric cDNA is positioned between the human cytomegalovirus immediate-early promoter-enhancer (Stenberg et al., 1984) and the polyadenylation-transcriptional termination sequences from SV40 to form a complete transcriptional unit.

The pACCMVapoA-1 plasmid (10 μg) was cotransfected into 293 cells with 5 μg of pJM17 (McGrory et al., 1988), a plasmid containing a full-length adenovirus 5 genome, by calcium phosphate coprecipitation using a glycerol shock to boost transfection efficiency. Homologous recombination between these plasmids results in the formation of a recombinant adenovirus genome of packageable size in which the CMVapoA-1 fusion gene replaces the native adenovirus early region 1. The adenovirus E1A gene product, required for expression of native adenoviral genes, is supplied in trans from a copy of early region 1 integrated into the 293 cell genome (Graham et al., 1977). Thus, in 293 cells, the recombinant viral genome is efficiently replicated and packaged into infectious viral particles.

Following transfection, monolayers of 293 cells were overlaid with 0.65% noble agar in Dulbecco's Modified Eagle medium (GIBCO) supplemented with 2% fetal bovine serum (Hyclone). Plaques representing foci of lytic infection became visible 8–15 days following transfection, and agar plugs containing the plaques were picked using a sterile Pasteur pipette. Plugs were suspended in 0.5 ml DME, subjected to one freeze-thaw cycle, and the resulting suspension (plaque lysate) used to infect fresh, confluent monolayers of 293 cells. Infected cells were incubated until extensive cytopathic effect was observed.

The identity of recombinant viruses was determined by restriction analysis and Southern blotting of viral DNA prepared from productively infected 293 cells. Infected monolayers were lysed in 0.6% SDS, 10 mM EDTA, pH 8.0, and digested with 20 μg/ml Proteinase K for 1 hour at 37° C. High molecular weight DNA was precipitated by the addition of 0.25 volumes 5 M NaCl and incubation on ice for 16 hours, and pelleted by centrifugation at 12,000×g for 15 minutes at 4° C. DNA was purified from the supernatant by phenol/chloroform extraction and ethanol precipitation. Following digestion with appropriate restriction endonucleases, viral DNA was electrophoresed in 1% agarose gels, and transferred to nylon membranes (Nytran, Schleicher and Schuell) by capillary blotting. Blots were hybridized with probes labeled with $^{32}P$ by oligonucleotide-primed synthesis from the parental plasmid DNA. Hybridized blots were imaged using a Molecular Dynamics Phosphorimager and ImageQuant software to demonstrate the presence of the appropriate insert.

The recombinant adenovirus AdRR5, which lacks an inserted gene in the E1 position, was generated from pACRR5 (Alcorn et al., 1993) and pJM17 in the same manner. The plasmid pACCMVtPA was constructed by ligating the XbaI fragment encoding human tissue plasminogen activator from pST$_7$tPA (Madison et al., 1989) into XbaI digested pACMVpLPA, and the resulting plasmid was employed to generate the recombinant adenovirus AdCMVtPA. Generation of AdCMVLuc, a recombinant adenovirus encoding firefly luciferase, has been described in Example 1, supra.

2. Preparation of Purified Viral Stocks

Secondary stocks of the recombinant virus were produced by infection of confluent monolayers of 293 cells grown in 10 cm tissue culture dishes. Monolayers were infected by addition of primary virus stock directly to culture plates. Infected cells were incubated at 37° C. until >90% of the cells showed cytopathic effect, then lysed by one freeze-thaw cycle before the medium/lysate was collected.

Large scale production of recombinant adenovirus was performed essentially as described previously (Herz et al., 1993, and U.S. Ser. No. 07/968,861; Green et al., 1979) by infecting confluent monolayers of 293 cells grown in 15 cm tissue culture plates with primary stock at a multiplicity of infection of 0.1–1.0. Infected monolayers were lysed with NP40 (final concentration 0.1%) when >90% of the cells showed cytopathic changes. Virus-containing extracts were centrifuged at 12,000×g for 10 min at 4° C. to remove cellular debris. Viral particles were precipitated by the addition of 0.5 volumes of 20% polyethylene glycol (PEG) 8000, 2.5 M NaCl and incubation on ice for 1 hour. Precipitated virus was collected by centrifugation at 12,000×g for 20 min. The resulting pellet was resuspended in 20 mM Tris HCl, pH 8.0, containing CsCl ($\rho$=1.1 gm/ml), layered over a discontinuous $\rho$=1.3 gm/ml–$\rho$=1.4 gm/ml density gradient, and centrifuged for 2 hours at 20,000 rpm in a Sorvall TH641 rotor at 4° C.

Recombinant virus was harvested from the 1.3–1.4 interface and desalted by chromatography on SEPHAROSE CL4B in an isotonic saline buffer (10 mM Tris HCl pH 7.4, 137 mM NaCl, 5 mM KCl, 1 mM $MgCl_2$). Purified virus eluting in the void volume was collected and, after addition of sterile bovine serum albumin to a final concentration of 0.1 mg/ml, snap frozen in liquid $N_2$ and stored at –80° C. until used. The titer of infectious viral particles in purified stocks was determined by plaque assay in monolayers of 293 cells (Green et al., 1979). Purified viral stocks of $>10_{10}$ plaque forming units/ml were routinely obtained.

EXAMPLE 7

EXPRESSION OF HUMAN AdCMVapoA-I IN INFECTED CELLS

This example describes the expression of the recombinant human apolipoprotein A-1 in tissue cultured cells.

1. Infection of Cultured Cells

CV-1 cells were cultured in 10 cm tissue culture dishes in Dulbecco's Modified Eagle medium (DMEM, GIBCO) supplemented with 10% fetal bovine serum (FBS Hyclone), and infected by the addition of various amounts of virus diluted into 1.5 ml of serum-free media directly to the culture plates. Duplicate 10 cm plates were infected for 1 hour with $10^7$, $10^8$, and $10^9$ pfu AdCMVapoA-I (multiplicities of infection of approximately 1, 10, and 100). As a control, duplicate plates were infected with AdCMVtPA at MOI of 10 or were mock-infected with serum-free media alone. Following 1 hour of exposure to virus the infecting media was aspirated and the cells reincubated in DMEM supplemented with 10% FBS. After 24 hours, medium was replaced with 8 ml serum-free DMEM supplemented with 250 4 μg/ml penicillin and 50 μg/ml streptomycin for 10 days at 37° C. Aliquots of conditioned media were obtained at various intervals after infection for determination of apolipoprotein A-I concentration.

2. Immunoprecipitation of Apolipoprotein A-I

Human apolipoprotein A-I was immunoprecipitated from medium conditioned by AdCMVapoA-I infected and control CV-1 cells using a commercially available goat anti-human apoA-I antibody (SIGMA). Precipitated protein was electrophoresed on SDS-15% polyacrylamide gels, and stained with Coomassie blue.

3. Analysis of apoA-I RNA

Total cellular RNA was prepared from uninfected and AdCMVapoA-I infected CV-1 Cells (48 hours after infection, MOI approximately 100) using the RNA STAT-60 reagent as directed by the supplier (Tel-Test "B"). Purified RNA (20 μg) was size fractionated by electrophoresis in formaldehyde/1% agarose gels, capillary blotted to nylon membrane (Nytran, Schleicher and Scheull), and hybridized against human apoA-I sequences uniformly labeled with $^{32}$P by oligonucleotide primed synthesis. Hybridized blots were imaged using a Molecular Dynamics Phosphorimager and ImageQuant software.

4. Results

Figure 8:
FIG. 8 is a Northern blot analysis of RNA isolated from uninfected and AdCMVapoA-I infected CV-1 cells. Total cellular RNA (20 µg) was size-fractionated by electrophoresis in formaldehyde-1% agarose, transferred to nylon membrane, and probed for human apoA-I sequences with a fragment of the human apoA-I cDNA uniformly labeled with $^{32}P$ by oligonucleotide-primed synthesis.

To determine whether cells infected with AdCMVapoA-I would synthesize and secrete human apoA-I, CV-1 cells cultured in 100 mm tissue culture dishes were infected with $10^7$, $10^8$, and $10^9$ pfu (corresponding multiplicities of infection of approximately 1, 10, and 100). Northern blotting of total cellular RNA isolated 48 hours after infection demonstrated expression of a single species of RNA (approximately 1.2 kb in size) hybridizing to the human apolipoprotein A-I probe. RNA from uninfected cells demonstrated no hybridization (FIG. 8).

Figure 9:
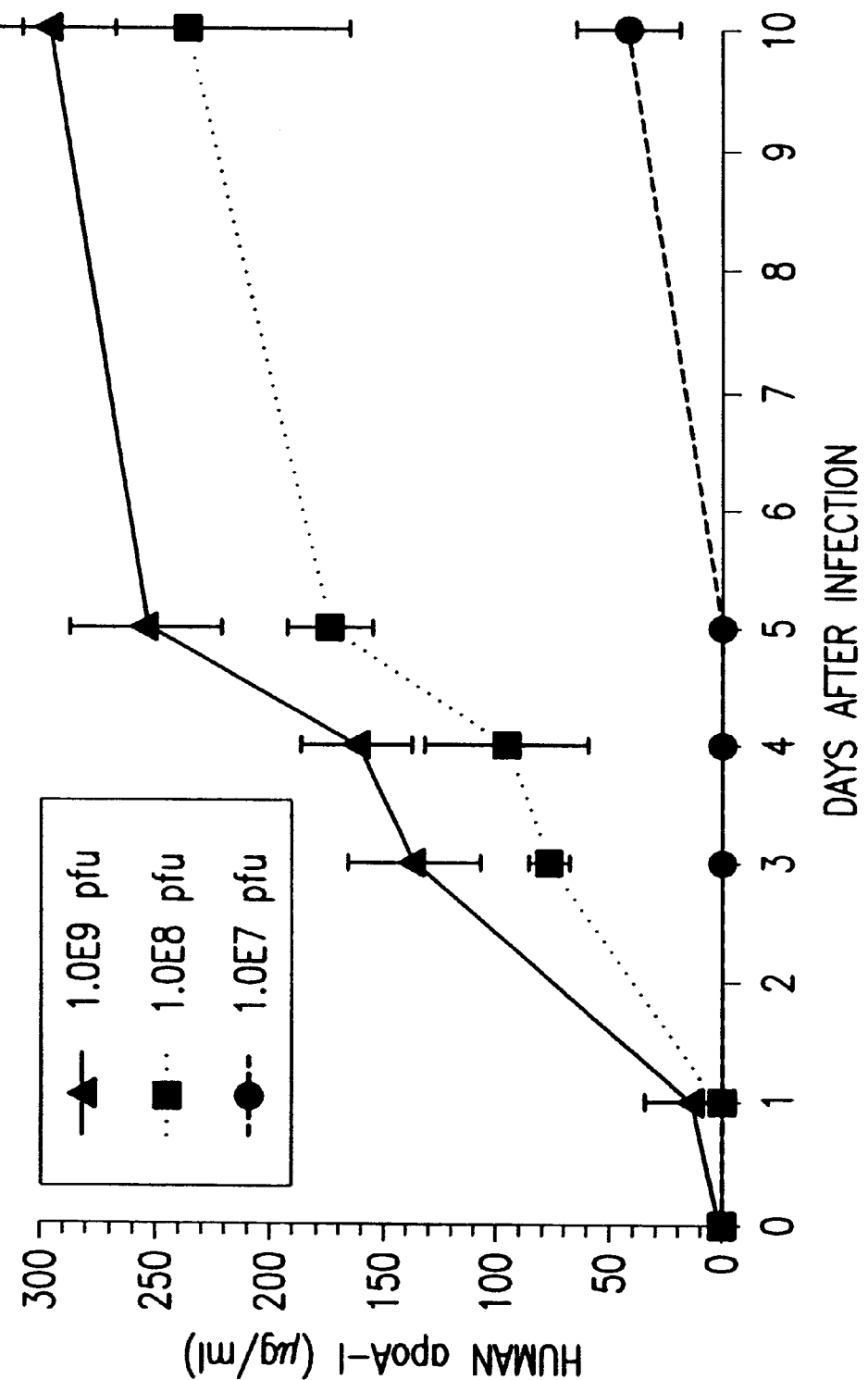
FIG. 9 demonstrates the accumulation of human apolipoprotein A-I in medium conditioned by CV-1 cells infected with AdCMVapoA-I. CV-1 cells were infected with AdCMVapoA-I at multiplicities of infection of approximately 1, 10 and 100. At the indicated intervals, aliquots of conditioned medium were removed and assayed for apoA-I using a commercial immunoturbidimetric assay. Medium conditioned by mock-infected cells or CV-1 cells infected with the control virus AdCMVtPA at a multiplicity of 10 secreted no detectable human apoA-I in the conditioned media at any time point.

Time and dose dependent accumulation of immunoreactive human apolipoprotein A-I was observed in medium conditioned by AdCMVapoA-I infected, but not control cells (FIG. 9). Cells infected at a multiplicity of infection of 100 secreted immunoreactive apoA-I protein at a rate of approximately 47 μg/$10^6$cells/24 h over a 10 day period following infection.

EXAMPLE 8

EXPRESSION OF HUMAN AdCMVapoA-I IN INFECTED MICE

This example describes the in vivo expression of human apolipoprotein A-1 in mice and the presence of the recombinant protein in the serum of the mice.

1. Animal Studies

Female BALB/c mice were anesthetized by intraperitoneal injection of 200 μg of Nembutal. An internal jugular vein was exposed through a combination of sharp and blunt dissection, and 0.1–0.25 ml of purified recombinant adenovirus stocks (approximately 1×$10^9$ pfu/ml) was injected intravenously using a tuberculin syringe under direct visualization. Hemostasis was obtained by direct pressure, and the incision closed with wound clips. Animals were allowed to recover on a warming tray before being returned to cages where they were provided with food and water ad libitum.

Samples of tail blood were obtained from reanesthetized animals at varying intervals after infection for determination of circulating apolipoprotein A-I and cholesterol levels. After 1–26 days, animals were sacrificed by intraperitoneal injection of 2 mg of Nembutal and exsanguinated. In addition, livers were harvested from some animals for isolation of nucleic acids or histologic analysis.

2. Immunoprecipitation of Apolipoprotein A-I

Human apolipoprotein A-I was immunoprecipitated from AdCMVapoA-I infected mice using a commercially available goat anti-human apoA-I antibody (SIGMA). Precipitated protein was electrophoresed on SDS-15% polyacrylamide gels, and stained with Coomassie blue.

3. Analysis of AdCMVapoA-I RNA in Liver from Infected Animals

Total cellular RNA was prepared from homogenized liver samples obtained from AdRR5 and AdCMVapoA-I infected mice. Purified RNA (20 μg) was size fractionated by electrophoresis in formaldehyde/1% agarose gels, capillary blotted to nylon membrane (Nytran, Schleister and Scheull), and hybridized against human apoA-I sequences uniformly labeled with $^{32}$P by oligonucleotide primed synthesis. Hybridized blots were imaged using a Molecular Dynamics Phosphorimager and ImageQuant software.

4. Results

To determine whether infection of intact animals with AdCMVapoA-I would result in accumulation of human apoA-I protein in serum, 13 BALB/C -mice were infected by intravenous injection of purified virus. High levels of human apoA-I were detected in serum from infected mice one day (251 mg/dl+/−103, n=6) and 5 days (Table 2) after infection. Serum from uninfected animals, or from animals infected with the irrelevant recombinant adenoviruses AdCMVLuc and AdRR5, demonstrated no immunoreactive material detectable above background (<5 mg/dl), confirming that the endogenous murine protein did not significantly cross-react in the immunoturbidometric assay. Similarly high levels of human apoA-I were observed in C57B/6 mice infected with AdCMVapoA-I.

TABLE 2

Human apolipoprotein A-1 and Lipids in Control and Infected Mice*

| | Human Apolipo-protein A-1 (mg/dl) | HDL Cholesterol (mg/dl) | Total Cholesterol (mg/dl) | Tri-glycerides (mg/dl) |
|---|---|---|---|---|
| AdCMVapoA-1 Infected Mice (n = 13) | 168 ± 68$^{a,b}$ | 77 ± 14$^{a,b}$ | 135 ± 33$^{a,b}$ | 199 ± $^{a,b}$ |
| Control Infected Mice (n = 9) | 2 ± 3$^c$ | 57 ± 7$^c$ | 92 ± 9$^c$ | 97 ± 41$^c$ |
| Uninfected Mice (n = 10) | 1 ± 1 | 64 ± 8 | 87 ± 12 | 125 ± 40 |

Figure 10:
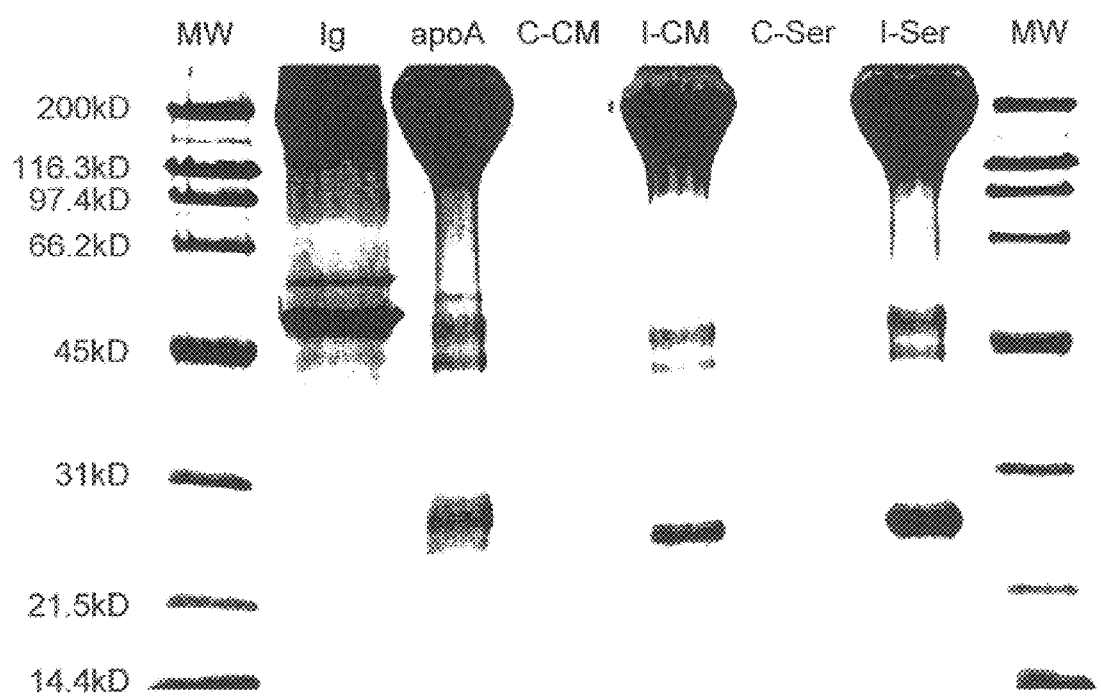
FIG. 10 illustrates the immunoprecipitation of human apolipoprotein A-I. Aliquots of conditioned medium or mouse serum were incubated with goat anti-human apolipoprotein A-I antiserum. Precipitated protein was collected by centrifugation, separated by electrophoresis in an SDS-15% polyacrylamide gel and stained with Coomassie blue. Lanes: MW: molecular weight standards; Ig: Commercial (SIGMA) anti-human apolipoprotein A-I antiserum; ApoA: immunoprecipitated purified human apolipoprotein A-I; C-CM: medium conditioned for 5 days by uninfected CV-1 cells; ICM: medium conditioned for 5 days by CV-1 cells following infection with AdCMVapoA-I; C-SER: serum from a mouse 5 days after infection with AdRR5; I-SER: serum from a mouse 5 days after infection with AdCMVapoA-I. The arrow indicates the position (28 kD) at which human apolipoprotein A-I migrates.

*Values are expressed as mean ± standard deviation.
$^a$p ≤ 0.01 versus uninfected mice
$^b$p ≤ 0.01 versus control infected mice
$^c$p = NS versus uninfected mice SDS-polyacrylamide gel electrophoresis of protein immunoprecipitated from serum of infected mice, and from medium conditioned by AdCMVapoA-I infected CV-1 cells, by goat anti-human apoA-I antiserum revealed a 28 kD band comigrating with the authentic human protein (FIG. 10).

Figure 11:
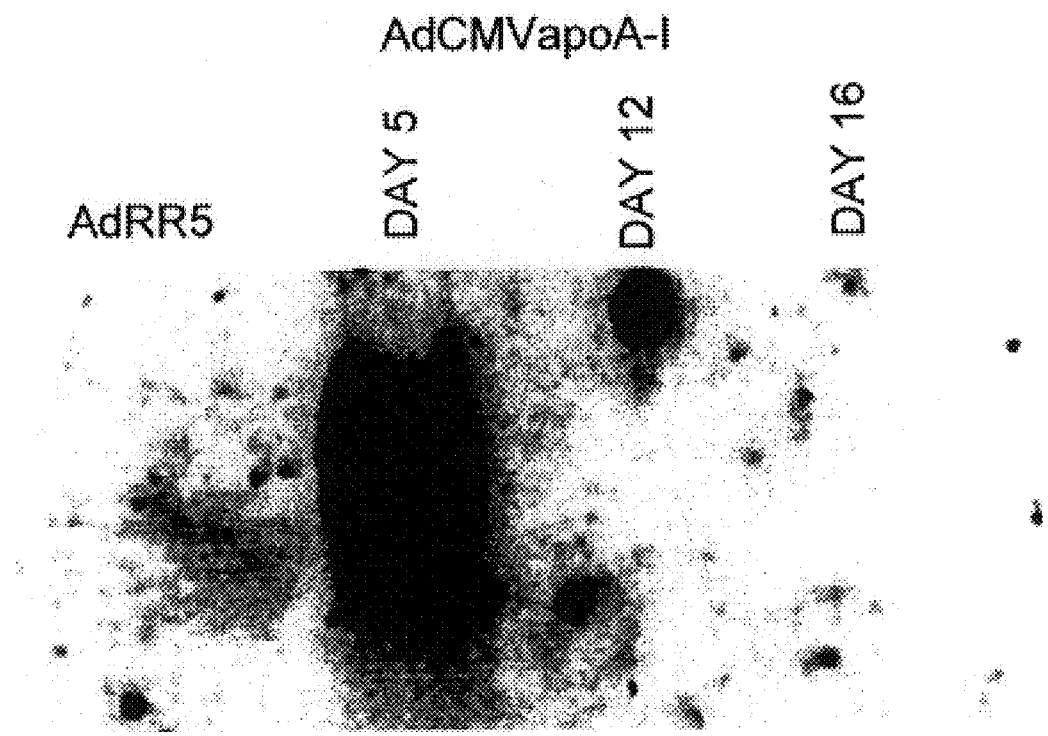
FIG. 11 is a Northern blot of mouse liver RNA. Total cellular RNA was isolated from the livers of mice 5, 12 or 26 days after infection with AdCMVapoA-I, or 5 days after infection with AdRR5, separated by electrophoresis in formaldehyde-1% agarose gels, transferred to nylon membrane and probed for human apolipoprotein A-I sequences with a fragment of the human apoA-I cDNA uniformly labeled with $^{32}p$ by oligonucleotide-primed synthesis.

While high levels of recombinant human apolipoprotein A-1 were observed in mice 5 days after infection, levels declined to <10% of maximal by 12 days after infection, and were essentially undetectable at 21 days. Northern blotting of RNA isolated from the livers of mice 5, 12 and 26 days after infection with AdCMVapoA-I confirmed that expression of the foreign gene was extinguished at the later times (FIG. 11).

EXAMPLE 9

EXPRESSION OF HUMAN ApoA-I INCREASES HDL CHOLESTEROL

This example describes the effects of circulating human apolipoprotein A-1 on the serum of mice.

1. Lipoprotein Fractionation

Pooled serum from groups of uninfected, AdRR5 infected and AdCMVapoA-I infected mice was brought to a density of 1.21 g/ml by the addition of solid KBr, layered over a cushion of 1.21 g/ml KBr, and centrifuged for 10 hours at 35,000 rpm and 4° C. in a Sorvall TH641 rotor (Havel et al., 1955; Hatch, 1968). The lipoprotein fractions were collected from the top of the density buffer, and chromatographed on a SUPEROSE 6 column essentially as previously described (Ha et al., 1985). Absorbance of the column eluate at 280 nm was monitored continuously, and 0.5–1 ml fractions collected for determination of apolipoprotein A-I, total protein, cholesterol, and triglyceride concentrations.

2. Assay Procedures
(a) Apolipoprotein A-I

Apolipoprotein A-I concentrations in conditioned medium and serum samples were determined using a commercially available immunoturbidometric assay (SIGMA) with minor modifications. Aliquots (5 µl) of each sample were mixed with 50 µl of the antibody reagent (goat anti-human apolipoprotein A-I) in 96 well flat bottom ELISA plates (CORNING), and incubated for 15 min at room temperature. For determining lower concentrations of apoA-I (after lipoprotein flotation and chromatographic fractionation) 50 µl of sample was mixed with 50 µl of antibody reagent. The absorbance was read at 340 nm on a Molecular Devices Thermomax plate reader and analyzed using Softmax software. All apoA-I determinations were performed in duplicate. Standard curves were constructed from apoA-I standards provided by the kit supplier.

(b) Cholesterol

Cholesterol levels in serum were determined using a commercially available cholesterol oxidase based assay kit (SIGMA), by a modification of the assay protocol suggested by the supplier. Aliquots (5 µl) of serum samples were mixed with 100 µl of the enzyme reagent in 96 well flat-bottom microtiter plates, and incubated at 37° C. for 5 minutes. For determining lower concentrations of cholesterol, 100 µl sample was mixed with 100 µl of reagent. Absorbance was read at 490 nm in the Molecular Devices plate reader and analyzed using Softmax software in comparison to standard curves generated using commercial cholesterol standards. All assays were performed in duplicate.

(c) HDL Cholesterol

The concentration of HDL cholesterol in serum samples was determined in the same assay following selective precipitation of low and intermediate density lipoproteins. Aliquots (20 µl) of serum were incubated with 4 µl of phosphotungstic acid in 96 well microtiter plates for 5 min at room temperature, and precipitated lipoproteins pelleted by centrifugation for 10 min at 3000 rpm in a Sorvall RT6000. The resulting supernatant was assayed for cholesterol as described.

(d) Triglycerides

Serum triglycerides were determined using a commercially available enzymatic assay (SIGMA). Aliquots (5 µl) of serum were incubated with 50 µl of fresh enzyme reagent for 10 min at 37° C. in 96 well microtiter plates, and the absorbance at 490 nm determined in the plate reader. For lower concentrations of triglyceride, 50 µl of sample was mixed with 50 µl of reagent. All assays were done in duplicate and compared to a standard curve constructed from the commercially supplied triglyceride standards.

3. Evaluation of Hepatotoxicity

Gamma-glutamyl transpeptidase, aspartate aminotransferase and serum bilirubin levels were similarly determined using commercially available kits (SIGMA) according to protocols provided by the supplier, modified only by scaling volumes for microtiter plate assays. Absorbance in these assays was determined using a Molecular Devices microtiter plate reader and Softmax software, and quantified by comparison against commercial standards.

4. Histopathology

Sections of liver were obtained from mice at various intervals after infection with AdCMVapoA-I were fixed in 0.25% glutaraldehyde in phosphate buffered saline for 24 hours, embedded in paraffin, sectioned, and stained with hematoxylin and eosin for photomicrography.

5. Data Analysis

Serum levels of human apolipoprotein A-I, serum lipid concentrations and circulating enzyme activities were compared using a two-tailed T test assuming unequal variances. For all determinations, significance was assumed for $P<0.05$.

6. Results

To determine whether expression of human apolipoprotein A-I produced a significant alteration in circulating lipids, apoA-I, total and high-density lipoprotein cholesterol and triglycerides were assayed in serum samples obtained from uninfected animals and from mice infected with $1\times10^9$ pfu AdCMVapoA-I or control viruses 5 days after infection (Table 2). Total serum cholesterol was approximately 47% greater in AdCMVapoA-I infected than control mice. High density lipoprotein cholesterol levels, determined after selective precipitation of other lipoproteins with phosphotungstic acid, were approximately 35% greater in AdCMVapoA-I infected animals. These results are similar to those previously observed in mice transgenic for a copy of the human apolipoprotein A-I gene (Rubin et al., 1991; Walsh et al., 1989; Sorci-Thomas et al., 1988; Rubin et al., 1991).

Figure 12:
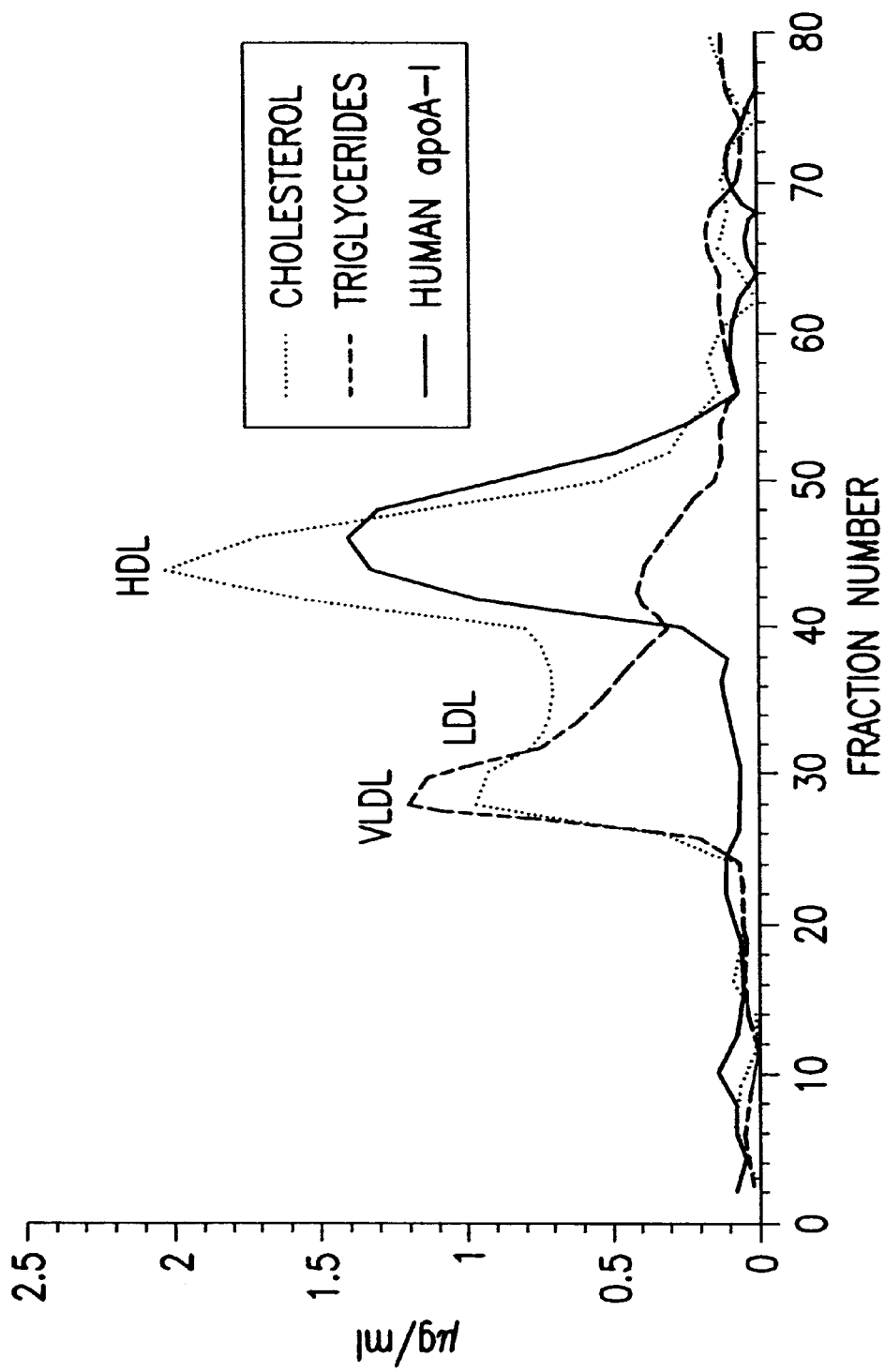

To further examine alterations in serum lipoproteins induced by overexpression of apoA-I, pooled sera from uninfected mice, from animals infected with AdCMVapoA-I and from mice infected with AdRR5 was fractionated by KBr density gradient ultracentrifugation. Lipoprotein-containing fractions (density r<1.21 gm/ml) were further separated by chromatography on SUPEROSE 6, and fractions eluting from the column were assayed for protein, cholesterol and human apoA-I (FIG. 12). The human apoprotein co-eluted with the predominant cholesterol peak, suggesting incorporation of human apolipoprotein A-I into HDL particles of appropriate density and size.

Mice infected with AdCMVapoA-I also demonstrated an increase in serum triglycerides (199+/−81 mg/dl) at 5 days compared to control infected (97+/−41 mg/ml) or uninfected (125+/−40 mg/ml) mice, respectively (p≦0.01). Serum triglycerides in mice infected with either AdCMVLuc or AdRR5 averaged 97+/−41 mg/dl, a level not significantly different from levels in uninfected animals (mean 125+/−40 mg/dl). This suggests that the rise in serum triglycerides is related to overexpression of human apoA-I rather than infection with adenovirus.

In general, animals infected with lower doses of AdCMVapoA-I demonstrated smaller increases in serum triglycerides. The elution pattern of triglyceride containing lipoproteins from the SUPEROSE 6 column was not qualitatively different for serum from AdCMVapoA-I infected mice in comparison to uninfected or AdRR5 infected mice, although the levels of triglycerides eluting in the VLDL peak were increased.

EXAMPLE 10

HUMAN GENE TRANSFER PROTOCOLS

This prophetic example describes some of the ways in which the present invention is envisioned to be of use in the treatment of human disorders via gene therapy, such as, for example, in the treatment of familial hypercholesterolemia (FH), atherosclerosis or in reducing risks of cardiovascular disease by increasing the apolipoprotein A-1 level in a subject.

Human subjects for whom the medical indication for adenovirus-mediated LDL receptor gene transfer or increased expression of apoA-1 has been established would be tested for the presence of antibodies directed against adenovirus. If antibodies are present and the patient has a history of allergy to either pharmacological or naturally occurring substances, application of a test dose of on the order of $10^6$ to $10^8$ recombinant adenovirus under close clinical observation would be indicated.

Recombinant adenovirus expressing the LDL receptor or apolipoprotein A-1 is prepared and purified by any method that would be acceptable to the Food and Drug Administration for administration to human subjects, including, but not limited to cesium chloride density gradient centrifugation, and subsequently tested for efficacy and purity. Virus is administered to patients by means of intravenous administration in any pharmacologically acceptable solution, either as a bolus or as an infusion over a period of time. Generally speaking, it is believed that the effective number of functional virus particles to be administered would range from $5 \times 10^{10}$ to $5 \times 10^{12}$.

Patients would remain hospitalized during the trial for at least 48 hrs. to monitor acute and delayed adverse reactions. Serum cholesterol levels, possibly HDL cholesterol and triglyceride levels where appropriate, and liver function parameters would be monitored twice daily to follow the efficacy of the gene transfer and to test for possible adverse hepatic inflammatory reactions (a potential side effect).

Further possible follow-up examinations include obtaining of a liver biopsy in which the pattern of expression of the transferred gene could be directly assessed. This would also supply information about the number of hepatocytes that have taken up the transferred gene and about the relative promoter strength in the human liver. Based on the data obtained, adjustments to the treatment may be desirable. These adjustments might include adenovirus constructs that use different promoters or a change in the number of pfu injected to ensure a homogeneous infection of all hepatocytes without unphysiological overexpression of the recombinant gene. Although the latter is not considered as a potential danger to the patient, the aim of the gene transfer should generally be to adjust plasma LDL and HDL cholesterol levels within the normal range of physiological parameters.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for or teach methodology, techniques and/or compositions employed herein.

Alcorn J. L., Gao E., Chen Q., Smith M. E., Gerard R. D., Mendelson C. R. (1993) *Mol Endocrinol* 7:1072–1085

Anderson W. F. (1992) *Science* 256:808–810

Badimon J. J., Fuster V., Badimon L. (1992) *Circulation* 86 (Suppl III):III-86–III-94

Badimon J. J., Badimon L., Galvez A., Dische R., Fuster V. (1989) *Lab Invest* 60:455–461

Badimon J. J., Badirnon L., Fuster V. (1990) *J Clin Invest* 85:1234–1241

Ballay A., Levrero M., Buendia M-A., Tiollais P., Perricaudet M. (1985) *EMBO J* 4:3861–3865

Beisiegel, U., Schneider, W. J., Goldstein, J. L., Anderson, R. G. W., and Brown, M. S. (1981) *J. Biol. Chem.*, 256, 11923–11931

Berkner K. L. (1988) *BioTechniques* 6:616–629

Bilheimer, D. W., Grundy, S. M., Brown, M. S., and Goldstein, J. L. (1983) *Trans. Assn. Am. Phys.*, 96, 1–8

Bilheimer, D. W., Goldstein, J. L., Grundy, S. C., Starzl, T. E., and Brown, M. S. (1984) *N. Engl. J. Med.*, 311, 1658–1664

Bonnerot, C., Rocancourt, D., Briand, P., Grimber, G., and Nicolas, J. F. (1987) *Proc. Natl. Acad. Sci. USA*, 84, 6795–6799

Brown, M. S. and Goldstein, J. L. (1986) *Science*, 232, 34–47

Davis, C. G., Elhammer, A., Russell, D. W., Schneider, W. J., Kornfeld, S., Brown, M. S., and Goldstein, J. L. (1986) *J. Biol. Chem.*, 261, 2828–2838 deWet, J. R., Wood, K. V., deLuca, M., Helinski, D. R., and Subramani, S. (1987) *Mol. Cell. Biol.*, 7, 725–737

Dichek, D. A., Bratthauer, G. L., Beg, Z. H., Anderson, K. D., Newman, K. D., Zwiebel, J. A., Hoeg, J. M., and Anderson, W. F. (1991) *Som. Cell. Mol. Gen.*, 17, 287–301

Eisenberg S. (1984) *J Lipid Res* 25:1017–1058

Frolkis, V. V., Kordjum, V. A., Bogatskaya, L. N., Novikova, S. N., Shulzhenko, V. N., Kostetsky, I. E., Mozzhukhina, T. G., Potapenko, R. I., Sabko, V. E., Paramonova, G. I. and Shkapenko, A. L. (1991) *Arch. Gerontol. Geriatr.*, 13, 225–236

Gerard R. D., Meidell R. S. (1993) *Trends in Cardiovasc Med* 3:9–15

Ghosh-Choudhury, G. and Graham, F. L. (1987) *Biochem. Biophys. Res. Comm.*, 147, 964–973

Glueck C. J., Gartside P., Fallat R. W., Sielski J., Steiner P. M. (1976) *J Lab Clin Med* 88:941–957

Gluzman, Y., Reichl, H., and Solnick, D. (1982) in *Eukaryotic Viral Vectors* (Gluzman, Y., ed) pp. 187–192, Cold Spring Harbor Press, Cold Spring Harbor, N.Y.

Goldbourt U., Behar S., Reicher-Reiss J. A., Kaplinsky E., Graff E., Kishon Y., Caspi A., Weisbort J., Mandelzweig L., Abinader E., Aharon L., Baann S., David D., Flich M., Friedman Y., Kristal N., Leil N., Markiewicz W., Marmor A., Palant A., Pelled B., Rabinowitz B., Reisin L., Roguin N., Rosenfeld T., Schlesinger Z., Sherf L., Tzivim D., Zahavi I., Zion M., Brunner D., for the Benzafibrate Infarction Prevention Study Group (1993) *Am J Cardiol* 71:909–915

Goldstein, J. L., Kita, T., and Brown, M. S. (1983) *N. Engl. J. Med.*, 309, 288–295

Goldstein, J. L., Basu, S. K., and Brown, M. S. (1983) *Meth. Enzymol.*, 98, 241–260

Goldstein, J. L. and Brown, M. S. (1989) in *The Metabolic Basis of Inherited Disease* (Scriver, C. R., Beaudet, A. L., Sly, W. S., and Valle, D., eds) pp. 1215–1250, McGraw-Hill Publishing Co., New York, N.Y.

Gomez-Foix A. M., Coats W. S., Baque S., Alam T., Gerard R. D., Newgard C. B. (1992) *J Biol Chem* 267:25129–25134

Gordon D. J., Probstfield J. L., Garrison R. J., Neaton J. D., Castelli W. P., Knoke J. D., Jacobs J., Bangdiwala S., Tyroler H. A. (1989) *Circulation* 79:815

Graham F. L., Smiley J., Russel W. C., Nairn R. (1977) *J Gen Virol* 36:59–72

Green M., Wold W. S. M. (1979) *Methods Enzymol* 58:425–435

Ha Y. C., Barter P. J. (1985) *J Chromatography* 341:154–159

Hatch F. T. (1968) *Adv Lipid Res* 6:1–68

Havel R. J., Eder H. A., Bragdon J. H. (1955) *J Clin Invest* 34:1345–1353

Herz J., Gerard R. D. (1993) *Proc Natl Acad Sci* (USA) 90:2812–2816

Herz, J., Clouthier, D. E., and Hammer, R. E. (1992) *Cell* 71:411–421

Hofmann, S. L., Russell, D. W., Brown, M. S., Goldstein, J. L., and Hammer, R. E. (1988) *Science*, 239, 1277–1281

Jaffe, H. A., Danel, C., Longenecker, G., Metzger, M., Setoguchi, Y., Rosenfeld, M. A., Gant, T. W., Thorgeirsson, S. S., Stratford-Perricaudet, L. D., Perricaudet, M., Pavirani, A., Lecocq, J. -P., and Crystal, R. G. (1992) *Nature Genetics*, 1, 372–378

Karathanasis S. K., Zannis V. I., Breslow J. L. (1983) *Proc Natl Acad Sci* (USA) 80:6147–6151

Karathanasis S. K., Norum R. A., Zannis V. I., Breslow J. L. (1983) *Nature* 301:718–720

Karlsson, S., Van Doren, K., Schweiger, S. G., Nienhuis, A. W., and Gluzman, Y. (1986) *EMBO J.*, 5, 2377–2385.

Kay, M. A., Baley, P., Rothenberg, S., Leland, F., Fleming, L., Parker Ponder, K., Liu, T. -J., Finegold, M., Darlington, G., Pokorny, W., and Woo, S. L. C. (1992) *Proc. Natl. Acad. Sci. USA*, 89, 89–93

Kottke B. A., Sinsmeister A. R., Holmes Jr., D. R., Kneller R. W., Hallaway B. J., Mao S. J. T. (1986) *Mayo Clin Proc* 61:313–320

Krieger, M., Brown, M. S., and Goldstein, J. L. (1981) *J. Mol. Biol.*, 150, 167–184

Law S. W., Brewer Jr., H. B. (1984) *Proc Natl Acad Sci* (USA) 81:66–70

Lemarchand, P., Jaffe, H. A., Danel, D., Cid, M. C., Kleinman, H. K., Stratford-Perricaudet, L. D., Perricaudet, M., Pavirani, A., Lecocq, J.-P., and Crystal, R. G. (1992) *Proc. Natl. Acad. Sci. USA*, 89, 6482–6486

Lowry, O. H., Rosebrough, N. J., Farr, A. L., and Randall, R. J. (1951) *J. Biol. Chem.*, 193, 265–275

Ma, P. T. S., Gil, G., Südhof, T. C., Bilheimer, D. W., Goldstein, J. L., and Brown, M. S. (1986) *Proc. Natl. Acad. Sci. USA*, 83, 8370–8374

Madison E. L., Goldsmith E. J., Gerard R. D., Gething M-J. H., Sambrook J. F. (1989) *Nature* 339:721–724

Manninen V., Elo M. O., Frick M. H., Haapa K., Heinonen O. P., Heinsalmi P., Helo P., Huttunen J. K., Kaitaniemi P., Koskinen P., Maenpaa H., Malkonen M., Manttari M., Norola A., Pasternack A., Pikkarainen J., Romo M., Sjoblom T., Nikkila E. A. (1988) *JAMA* 260:641–651

McGrory W. J., Bautista D. S., Graham F. L. (1988) *Virology* 163:614–617

Miller A. D. (1992) *Nature* 357:455–457

Miller, D. G., Adam, M. A., and Miller, A. D. (1990) *Mol. Cell. Biol.*, 10, 4239–4242

Miller N. E. (1987) *Am Heart J* 113:589–597

Miller N. E. (1990) *Biochem Pharmacol* 40:403410

Ordovas J. M., Schaefer E. J., Salem D., Ward R. H., Glueck C. J., Vergani C., Wilson P. W., Karathanasis S. K. (1986) *N Engl J Med* 314:671–677

Peacock, S. L., Bates, M. P., Russell, D. W., Brown, M. S., and Goldstein, J. L. (1988) *J. Biol. Chem.*, 263, 7838–7845

Prevec L., Schneider M., Rosenthal K. L., Belbeck L. W., Derbyshire J. B., Graham F. L. (1989) *J Gen Virol* 70:429–434

Prince G. A., Porter D. D., Jenson A. B., Horswood R. L., Chanock R. M., Ginsberg H. S. (1993) *J Virol* 67:101–111

Reichl D., Miller N. E. (1986) *Clin Sci* 70:221–231

Rosenfeld, M. A., Yoshimura, K., Trapnell, B. C., Yoneyama, K., Rosenthal, E. R., Dalemans, W., Fukayama, M., Bargon, J., Stier, L. E., Stratford-Perricaudet, L. D., Perricaudet, M., Guggino, W. B., Pavirani, A., Lecocq, J. -P., and Crystal, R. G. (1992) *Cell*, 68, 143–155

Rosenfeld, M. A., Siegfried, W., Yoshimura, K., Yoneyama, K., Fukayama, M., Stier, L. E., Pääkkö, P. K., Gilardi, P., Stratford-Perricaudet, L. D., Perricaudet, M., Jallat, S., Pavirani, A., Lecocq, J. -P., and Crystal, R. G. (1991) *Science*, 252, 431–434

Roy Chowdhury, J., Grossman, M., Gupta, S., Roy Chowdhury, N., Baker, J. R., and Wilson, J. M. (1991) *Science*, 254, 1802

Rubin E. M., Krauss R. M., Spangler E. A., Verstuyft J. G., Clift S. M. (1991) *Nature* 353:265–267

Rubin E. M., Ishida B. Y., Clift S. M., Krauss R. M. (1991) *Proc Nati Acad Sci* (USA) 88:434–438

Rubins H. B., Robins S. J., Lwane M. K., Boden W. E., Elam M. B., Fye C. L., Gordon D. J., Schaefer E. J., Schectman G., Wittes J. T. (1993) *Am J Cardiol* 71:45–52

Sambrook, J., Fritsch, E. F., and Maniatis, T. (1989) *Molecular cloning: A laboratory manual*, Cold Spring Harbor Laboratory Press, New York Scharfmann R., Axelrod J. H., Verma I. M. (1991) *Proc Natl Acad Sci* (USA) 88:4626–4630

Sorci-Thomas M., Prack M. M., Dashit N., Johnson F., Rudel L. L., Williams D. L. (1988) *J Biol Chem* 263:5183–5189

Stenberg R. M., Thomsen D. R., Stinski M. F. (1984) *J Virol* 49:190–199

Stratford-Perricaudet, L. D., Makeh, I., Perricaudet, M., and Briand, P. (1992) *J. Clin. Invest.*, 90, 626–630

Stratford-Perricaudet, L. D., Levrero, M., Chasse, J. -F., Perricaudet, M., and Briand, P. (1990) *Hum. Gene Ther.*, 1, 241–256

Third J. L. H. C., Montag J., Flynn M., Freidel J., Laskarzewski P., Glueck C. J. (1984) *Metabolism* 33:136–146

Thomsen, D. R., Stenberg, R. M., Goins, W. F., and Stinski, M. F. (1984) *Proc. Natl. Acad. Sci. USA*, 81, 659–663

Towbin, H., Staehelin, T., and Gordon, J. (1979) *Proc. Natl. Acad. Sci. USA*, 76, 4350–4354 van Doren, K., Hanahan, D., and Gluzman, Y. (1984) *J. Virol.*, 50, 606–614 van Doren, K. and Gluzman, Y. (1984) *Mol. Cell. Biol.*, 4, 1653–1656

Vergani C., Bettale G. (1981) *Clin Chimica Acta* 114:45–52

Walsh A., Ito Y., Breslow J. L. (1989) *J Biol Chem* 264:6488–6494

Widom R. L., Ladias J. A. A., Kouidou S., Karathanasis S. K. (1991) *Mol Cell Biol* 11:677–687

Wilson, J. M., Jefferson, D. M., Roy Chowdhury, J., Novikoff, P. M., Johnston, D. E., and Mulligan, R. C. (1988) *Proc. Natl. Acad. Sci. USA*, 85, 3014–3018

Wilson, J. M., Johnston, D. E., Jefferson, D. M., and Mulligan, R. C. (1988) *Proc. Natl. Acad. Sci. USA*, 85, 4421–4425

Wilson, J. M., Grossman, M., Wu, C. H., Roy Chowdhury, N., Wu, G. Y., and Roy Chowdhury, J. (1992) *J. Biol. Chem.*, 267, 963–967

Wolfe, J. H., Deshmane, S. L., and Fraser, N. W. (1992) *Nature Genetics*, 1, 379–384

Yamamoto, T., Davis, C. G., Brown, M. S., Schneider, W. J., Casey, M. L., Goldstein, J. L., and Russell, D. W. (1984) *Cell*, 39, 27–38

Yokode, M., Pathak, R. K., Hammer, R. E., Brown, M. S., Goldstein, J. L., and Anderson, R. G. W. (1992) *J. Cell Biol.*, 117, 39–46

What is claimed is:

1. A method for increasing high density lipoprotein cholesterol in a mammal comprising administering to said mammal a pharmaceutical composition comprising an adenovirus vector construct comprising a human apoA-1 expression region recombinant insert, wherein said recombinant insert comprises a secretory signal sequence encoding DNA segment fused 5' to and in frame with a human apoA-1 encoding region, and wherein said vector expresses and secretes human apolipoprotein A-1 upon transfection into a mammalian cell, in an amount effective to increase high density hpoprotein cholesterol in said mammal.

2. The method of claim 1, wherein the administering is by means of an intravenous injection of from $5\times10^{10}$ to about $5\times10^{12}$ virus particles.

3. The method of claim 1, wherein said mammal is a mouse.

4. The method of claim 1, wherein said mammal is a human.

5. A method of increasing serum high density lipoprotein in a mammal comprising administering to said mammal an adenovirus vector construct comprising a human apoA-1 expression region recombinant insert, wherein said recombinant insert comprises a secretory signal sequence encoding DNA segment fused 5' to and in frame with a human apoA-1 encoding region, and wherein said vector expresses and secretes human apolipoprotein A-1 upon transfection into a mammalian cell, in an amount effective to increase serum high density lipoprotein in said mammal.

6. The method composition of claim 1, wherein said vector construct is packaged within a virion or virus particle.

* * * * *

UNITED STATES PATENT AND TRADEMARK OFFICE
CERTIFICATE OF CORRECTION

PATENT NO. : 6,503,498 B1
DATED : January 7, 2003
INVENTOR(S) : Gerard et al.

It is certified that error appears in the above-identified patent and that said Letters Patent is hereby corrected as shown below:

Column 35,
Line 28, please delete "hpoprotein" and insert -- lipoprotein -- therefor.

Signed and Sealed this

First Day of July, 2003

JAMES E. ROGAN
*Director of the United States Patent and Trademark Office*